United States Patent
Iwata

(10) Patent No.: US 8,575,564 B2
(45) Date of Patent: Nov. 5, 2013

(54) PARTICLE BEAM IRRADIATION APPARATUS AND PARTICLE BEAM THERAPY SYSTEM

(75) Inventor: Takaaki Iwata, Chiyoda-ku (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 0 days.

(21) Appl. No.: 13/076,651

(22) Filed: Mar. 31, 2011

(65) Prior Publication Data

US 2011/0240874 A1 Oct. 6, 2011

(30) Foreign Application Priority Data

Apr. 2, 2010 (JP) ................................. 2010-085993
Dec. 21, 2010 (JP) ................................. 2010-284520

(51) Int. Cl.
*A61N 5/10* (2006.01)
*H01J 3/14* (2006.01)

(52) U.S. Cl.
USPC .................................... 250/396 R; 250/492.3

(58) Field of Classification Search
USPC ........... 250/396 R–398, 400, 396 ML, 492.1, 250/492.3
See application file for complete search history.

(56) References Cited

U.S. PATENT DOCUMENTS

| | | | |
|---|---|---|---|
| 5,668,371 A * | 9/1997 | Deasy et al. | 850/1 |
| 7,026,636 B2 | 4/2006 | Yanagisawa et al. | |
| 7,977,657 B2 * | 7/2011 | Flynn et al. | 250/492.3 |
| 2004/0149934 A1 | 8/2004 | Yanagisawa et al. | |
| 2006/0017015 A1 * | 1/2006 | Sliski et al. | 250/492.3 |
| 2006/0226372 A1 * | 10/2006 | Yanagisawa et al. | 250/396 R |
| 2011/0105821 A1 * | 5/2011 | Dieter et al. | 600/1 |

FOREIGN PATENT DOCUMENTS

| | | |
|---|---|---|
| DE | 102007054919 A1 | 2/2009 |
| JP | 2001-61978 A | 3/2001 |
| JP | 2001-212253 A | 8/2001 |
| JP | 200469683 A | 3/2004 |

(Continued)

OTHER PUBLICATIONS

Sake Taira, IMRT with Combined Rotating and Fixed Multi-port Irradiation (Cutting Field IMRT). Medical Review No. 87 (2002), pp. 44-48.

(Continued)

*Primary Examiner* — Robert Kim
*Assistant Examiner* — David E Smith
(74) *Attorney, Agent, or Firm* — Buchanan Ingersoll & Rooney PC

(57) ABSTRACT

When the IMRT technology for a radiation therapy system utilizing an X-ray or the like is applied as it is to a particle beam therapy system having a conventional wobbler system, there is posed the problem that it is required to utilize two or more boluses. The objective of the present invention is to solve the problem of excess irradiation in IMRT by a particle beam therapy system. More specifically, the problem of excess irradiation in IMRT by a particle beam therapy system is solved by raising the irradiation flexibility in the depth direction, without utilizing a bolus.

There is provided a particle beam irradiation apparatus (58) having a scanning irradiation system (34) that performs scanning with a charged particle beam (1) accelerated by an accelerator and being mounted in a rotating gantry for rotating the irradiation direction of the charged particle beam (1); the particle beam irradiation apparatus (58) comprises a columnar-irradiation-field generation apparatus (4) that generates a columnar irradiation field by enlarging the Bragg peak of the charged particle beam (1).

18 Claims, 14 Drawing Sheets

(56) References Cited

FOREIGN PATENT DOCUMENTS

| JP | 2005-37214 A | | 2/2005 |
| JP | 2006341010 A | * | 12/2006 |
| JP | 2009-66106 A | | 4/2009 |
| WO | WO 2009/026997 A1 | | 3/2009 |

OTHER PUBLICATIONS

Emergency statement for Intensity-Modulate Radiotherapy. Jastro Newsletter 2002, 63(3), pp. 4-7.
Chinese Office Action issued May 27, 2013, in corresponding Application No. 201110874462.8 and English-language translation, 25 pps.
Taiwanese Office Action issued Jun. 21, 2013, in corresponding Application No. 100106835, 9 pps.

* cited by examiner

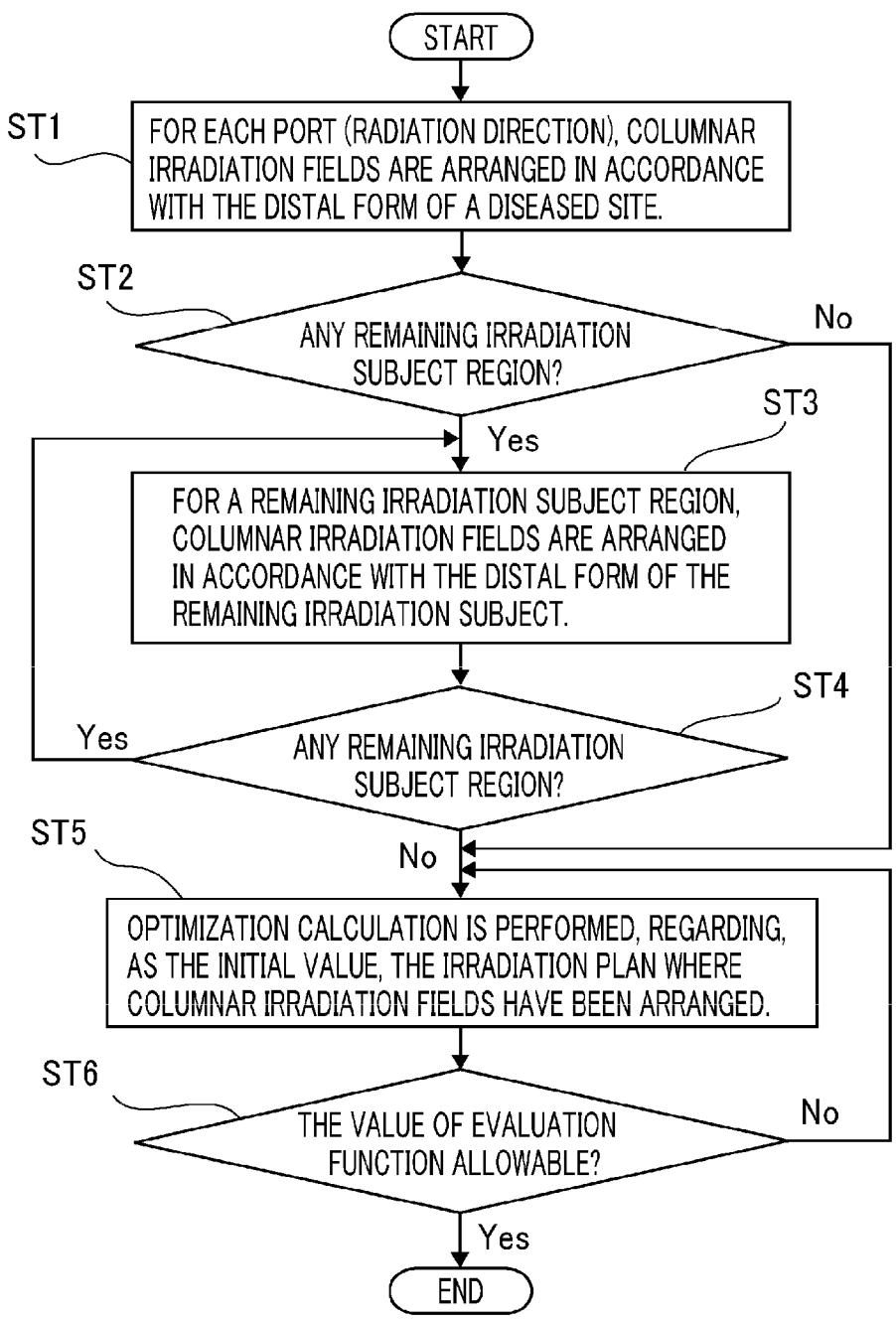

PARTICLE BEAM IRRADIATION APPARATUS AND PARTICLE BEAM THERAPY SYSTEM

BACKGROUND OF THE INVENTION

1. Field of the Invention

The present invention relates to a medical system (referred to as a "particle beam therapy system", hereinafter) that performs therapy by irradiating a charged particle beam (referred to as a "particle beam", hereinafter), exemplified by a heavy particle beam such as a carbon beam or a proton beam, onto the diseased site of a cancer or the like.

2. Description of the Related Art

Among medical systems that have been developed earlier than particle beam therapy systems and perform therapy by utilizing a radiation such as an X-ray, there has been proposed a medical system that performs therapy of a diseased site evenly with a high dose by irradiating radiations, whose intensity are adjusted, from many directions so that exposure of peripheral tissues is reduced. Here, irradiation onto a diseased site from many directions is referred to as multi-port irradiation.

A number of methods have been proposed for multi-port irradiation; they are exemplified, for example, by IMRT (Intensity-Modulated Radiotherapy: referred Documents 1 and 2 in non-patent document 1), which is proposed mainly by Siemens and in which "step and shoot" is performed, and IMAT (Intensity-Modulated Ark Therapy: referred Document 3 in non-patent document 1), which is proposed mainly by ELEKTA.

In Patent Document 1, there is proposed a radiation irradiation apparatus that is provided with a plurality of compensators for changing the spatial pattern of the X-ray intensity distribution for each irradiation direction so as to apply a high absorption dose only to a diseased site and that performs multi-port irradiation while automatically changing compensators in accordance with irradiation directions.

PRIOR ART REFERENCE

Patent Document

[Patent Document 1] Japanese Patent Application Laid-Open No. 2005-37214 (FIGS. 17 through 21)

Non-Patent Document

[Non-Patent Document 1] Sake Taira. IMRT with Combined Rotating and Fixed Multi-port Irradiation (Cutting Field IMRT). MEDICAL REVIEW NO. 87 (2002); PP. 44-48.

[Non-Patent Document 2] Emergency statement for Intensity-Modulated Radiotherapy. JASTRO NEWSLETTER 2002; 63(3): PP. 4-7.

With regard to a radiation therapy system utilizing an X-ray or the like, IMRT has been widely applied to clinical practices for a head and neck area, a prostate, and the like and has achieved a superior performance; on the other hand, the problem of excess irradiation has been pointed out. According to Non-Patent Document 2, it is warned that, depending on the contents of a treatment plan, IMRT eventually brings about a phenomenon that is caused by excess irradiation and is harmful to normal tissues, regardless of consciously increasing one-time dose or total dose, or on the contrary, there is caused a risk that underdose irradiation due to being conservative provides an insufficient treatment effect.

It is conceivable that one of the causes of the excess irradiation is insufficient irradiation flexibility. The final irradiation field of IMRT in the radiation therapy system utilizing an X-ray or the like described in any one of referred Documents 1 through 3 in non-patent document 1 and non-patent document 2 is realized by superimposing two or more irradiations on one another, utilizing as parameters (1) irradiation energy, (2) an irradiation angle, (3) a transverse-direction irradiation-field limitation through a multileaf collimator referred to as a "MLC", hereinafter) or the like, and (4) an irradiation dose (weight). In this case, no depth-direction irradiation-field limiter is utilized.

The depth-direction irradiation-field limiter is exemplified by a bolus utilized in a particle beam therapy system. The changing form of a diseased site in the depth direction is referred to as a distal form. A bolus is an energy modulator obtained by machining in accordance with this distal form; the energy modulator is formed by machining polyethylene or wax for each patient. An irradiation apparatus provided with a bolus is disclosed, for example, in FIG. 21 of Patent Document 1; this irradiation apparatus can make the shape of an irradiation field coincide with the distal form of a diseased site.

However, in a particle beam therapy system, a single bolus cannot be applied as it is to multi-port irradiation. At first, in the case of IMRT, it is required to prepare respective boluses for two or more irradiation directions. In the radiation irradiation apparatus disclosed in Patent Document 1, the compensator, which corresponds to a bolus, can automatically be moved; however, there has been a problem that machining of the bolus requires many labor hours and costs. In the case of IMAT, there has been another further difficult problem; it is required to automatically change the bolus shape in accordance with the irradiation angle that changes on a moment-to-moment basis. At present, this kind of dynamic shape change cannot be realized by a bolus.

Accordingly, when the IMRT technology for a radiation therapy system utilizing an X-ray or the like is applied as it is to a particle beam therapy system having a conventional wobbler system, there still exists the problem that it is required to utilize two or more boluses. It is not possible to limit the irradiation field in the depth direction without utilizing a bolus, i.e., it is not possible to raise the irradiation flexibility; therefore, it is impossible to solve the problem of excess irradiation without utilizing a bolus.

SUMMARY OF THE INVENTION

The objective of the present invention is to solve the foregoing problems. In other words, the objective of the present invention is to solve the problem of excess irradiation in IMRT by a particle beam therapy system. More specifically, the problem of excess irradiation in IMRT by a particle beam therapy system is solved by raising the irradiation flexibility in the depth direction, without utilizing a bolus.

There is provided a particle beam irradiation apparatus having a scanning irradiation system that performs scanning with a charged particle beam accelerated by an accelerator and being mounted in a rotating gantry for rotating the irradiation direction of the charged particle beam. The particle beam irradiation apparatus includes a columnar-irradiation-field generation apparatus that generates a columnar irradiation field by enlarging the Bragg peak of the charged particle beam.

The particle beam irradiation apparatus according to the present invention performs irradiation in such a way as to generate a columnar irradiation field, which is obtained by enlarging the Bragg peak of a charged particle beam, at the depth corresponding to the distal form of an irradiation subject; therefore, the problem of excess irradiation in IMRT by a particle beam therapy system can be solved by raising the irradiation flexibility in the depth direction, without utilizing a bolus.

The foregoing and other object, features, aspects, and advantages of the present invention will become more apparent from the following detailed description of the present invention when taken in conjunction with the accompanying drawings.

BRIEF DESCRIPTION OF THE DRAWINGS

FIG. 4 is a flowchart representing a method of generating a treatment plan utilized in a particle beam irradiation apparatus according to the present invention;

Figure 6A:
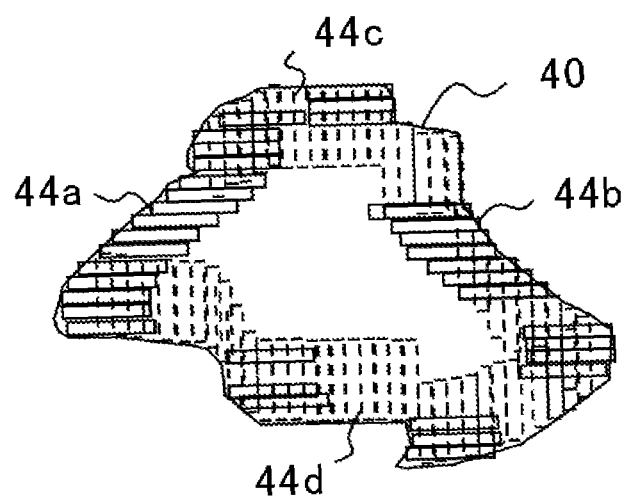
Figure 6B:
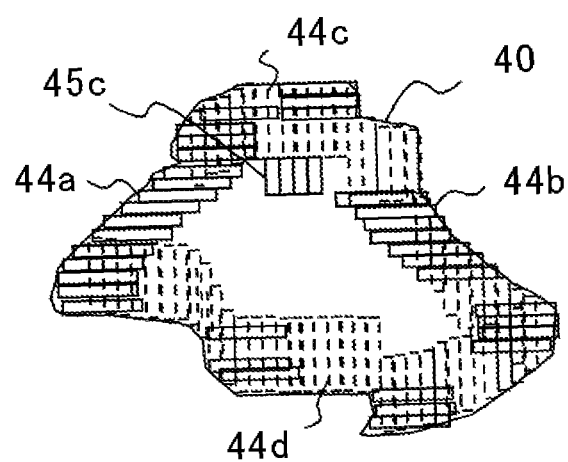
Figure 6C:
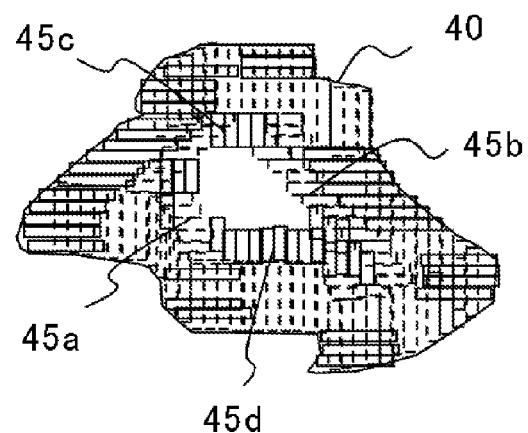
Figure 7:
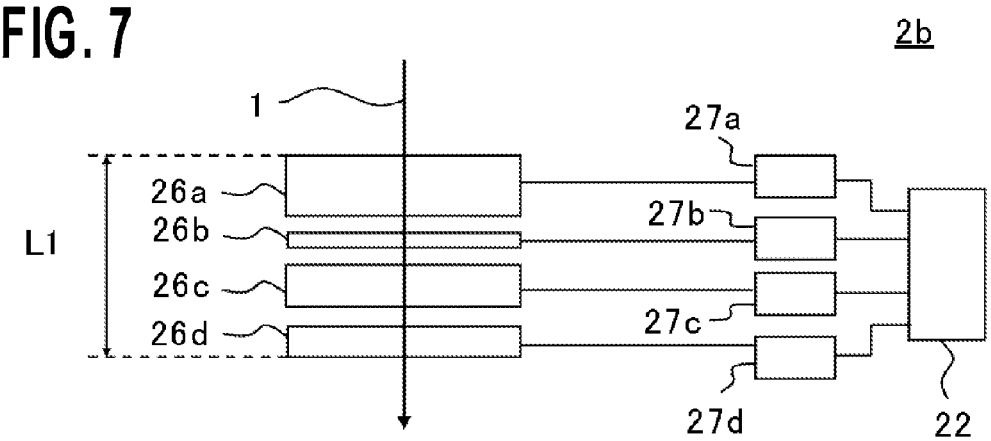
Figure 8:
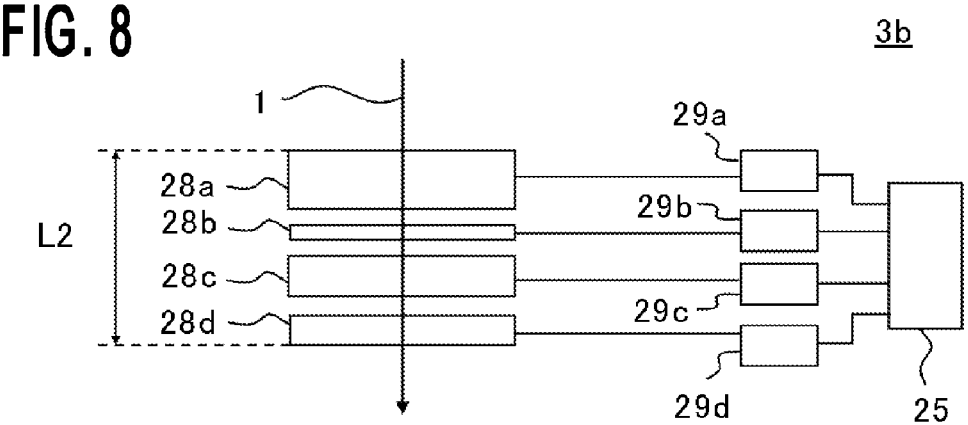
Figure 9:
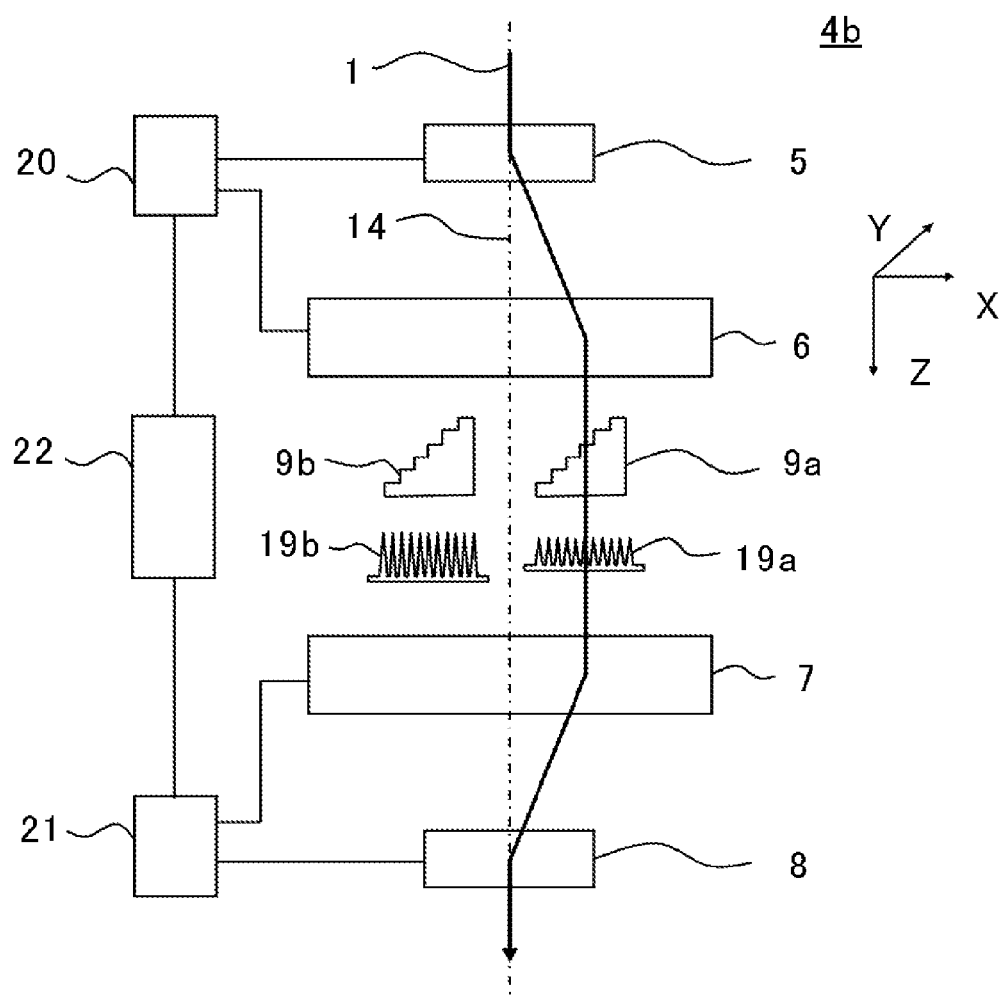
Figure 10:
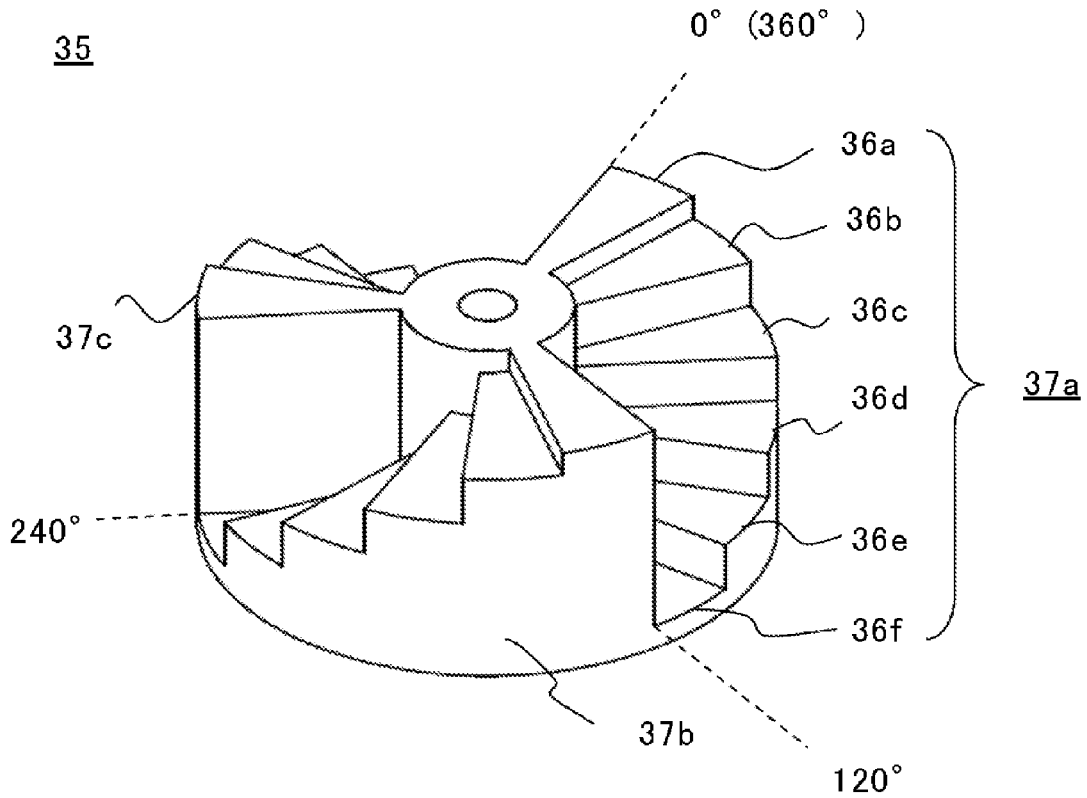
Figure 11:
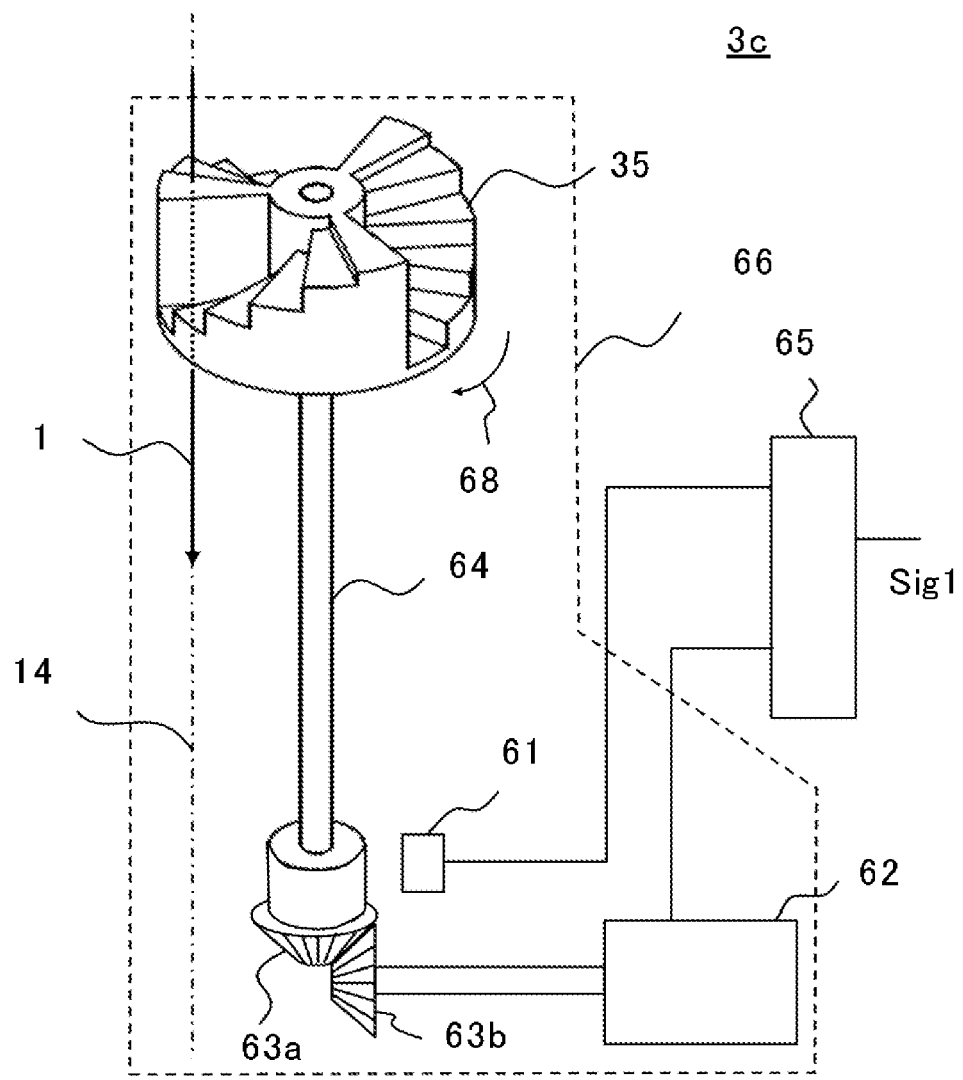
Figure 12:
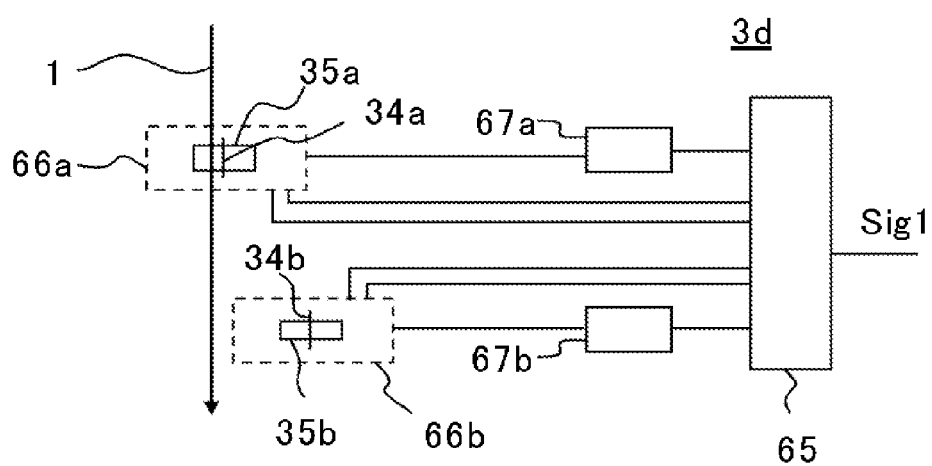
Figure 13:
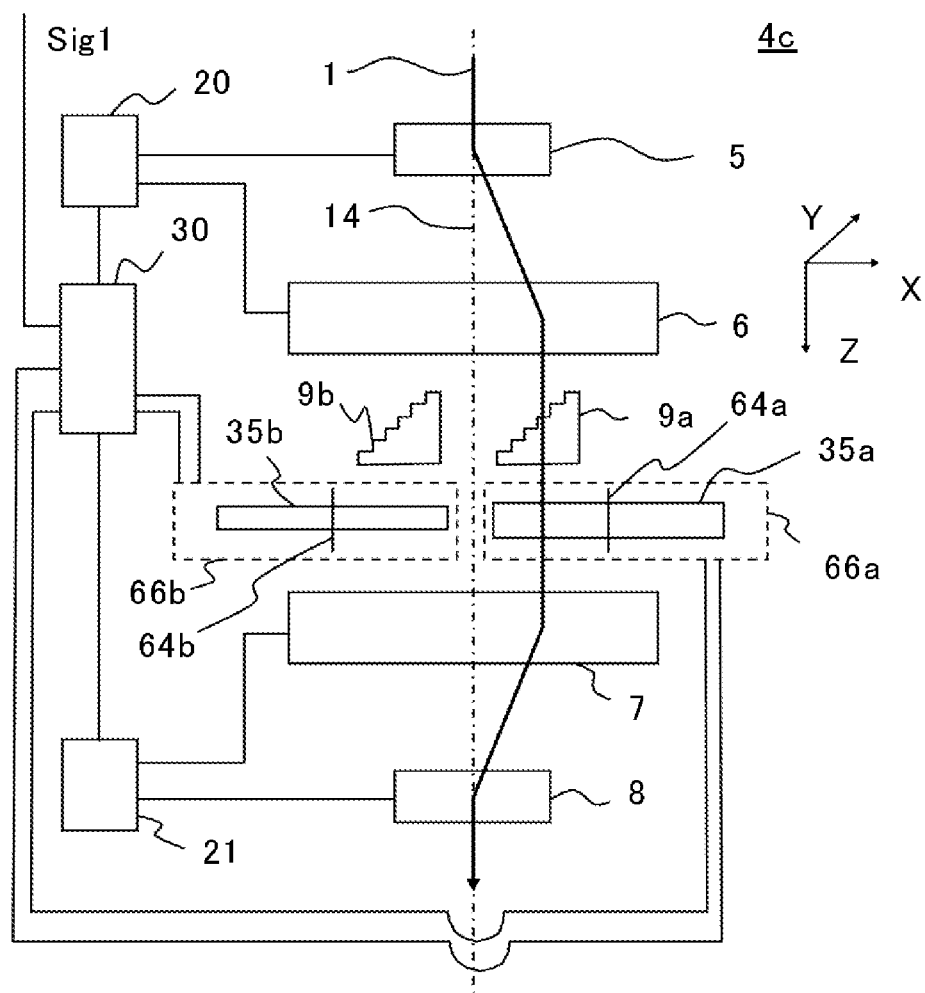
Figure 14:
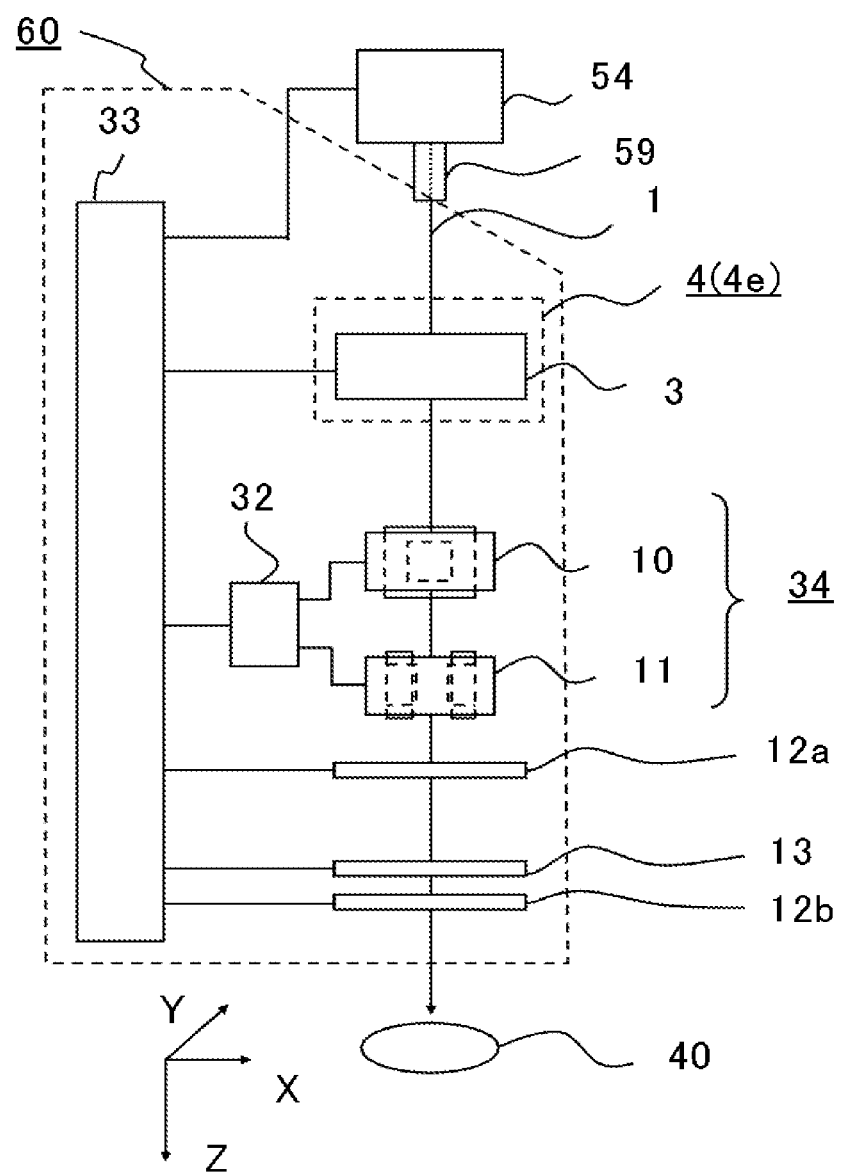
Figure 15:
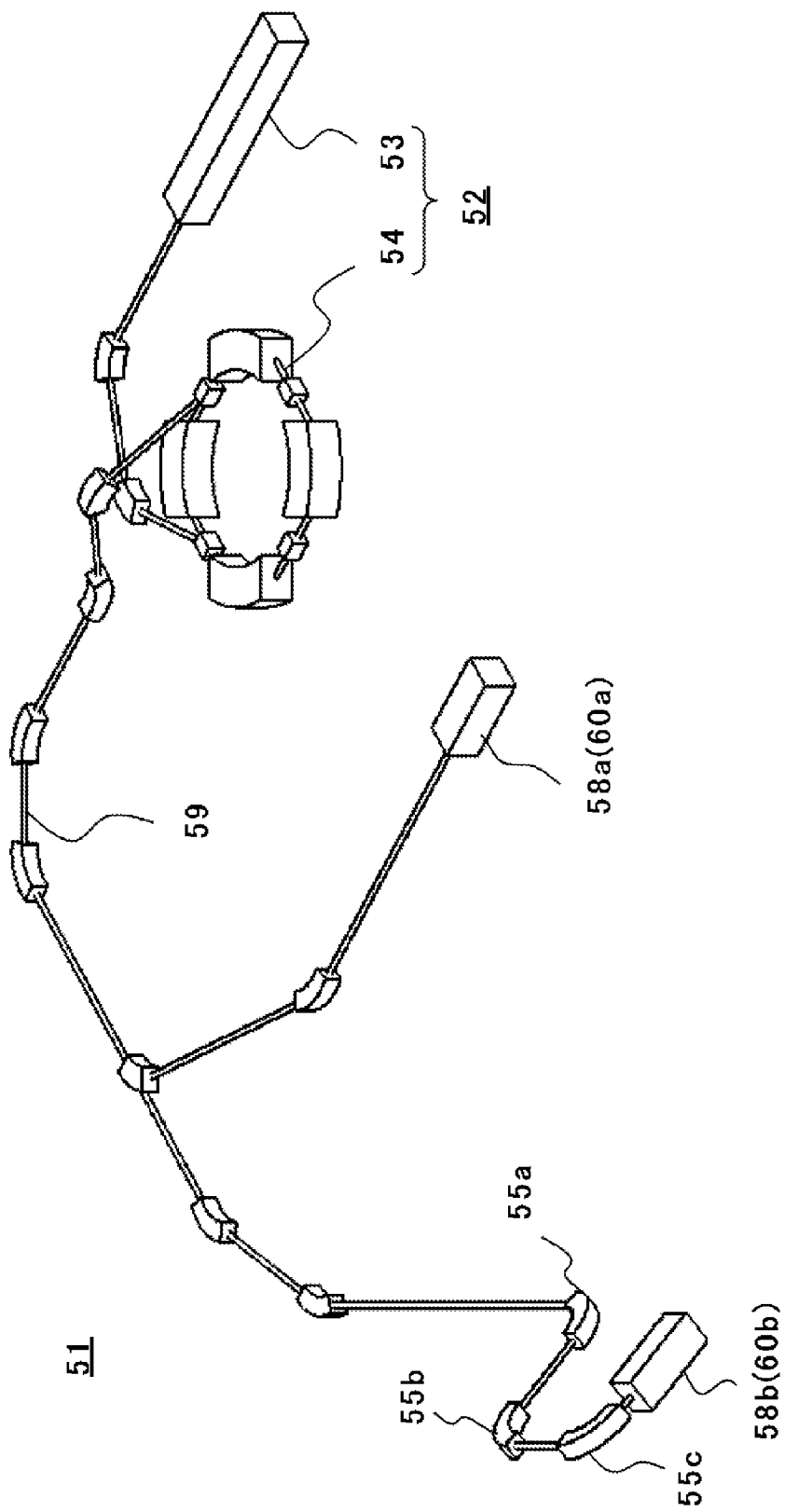

Each of FIGS. 5A through 5D is a view for explaining the step ST1 in FIG. 4;

Each of FIGS. 6A through 6C is a schematic diagram for obtaining the initial state in an optimum calculation, according to the present invention, for a treatment plan;

FIG. 7 is a configuration diagram illustrating an energy changing apparatus according to Embodiment 2 of the present invention;

FIG. 8 is a configuration diagram illustrating a depth-direction irradiation field enlargement apparatus according to Embodiment 3 of the present invention;

FIG. 9 is a configuration diagram illustrating a columnar-irradiation-field generation apparatus according to Embodiment 4 of the present invention;

FIG. 10 is an external view illustrating an RMW according to Embodiment 5 of the present invention;

FIG. 11 is a configuration diagram illustrating a depth-direction irradiation field enlargement apparatus according to Embodiment 5 of the present invention;

FIG. 12 is a configuration diagram illustrating a depth-direction irradiation field enlargement apparatus according to Embodiment 6 of the present invention;

FIG. 13 is a configuration diagram illustrating a columnar-irradiation-field generation apparatus according to Embodiment 7 of the present invention;

FIG. 14 is a configuration diagram illustrating a particle beam irradiation apparatus according to Embodiment 8 of the present invention; and FIG. 15 is a configuration diagram illustrating a particle beam therapy system according to Embodiment 9 of the present invention.

DETAILED DESCRIPTION OF THE PREFERRED EMBODIMENTS

Embodiment 1

There will be considered IMRT through columnar scanning irradiation, which is the feature of the present invention. In normal spot scanning, a beam spot is irradiated onto a diseased site in a three-dimensional manner, as if painting is performed in a pointillist manner. As described above, the spot scanning is a high-flexibility irradiation method; on the other hand, it takes a long time to perform irradiation onto the whole diseased site. IMRT takes a further long time because it is multi-port irradiation. Accordingly, by enlarging the BP (Bragg peak) in the depth direction comparison with the spot scanning, a columnar irradiation field is generated.

Figure 1:
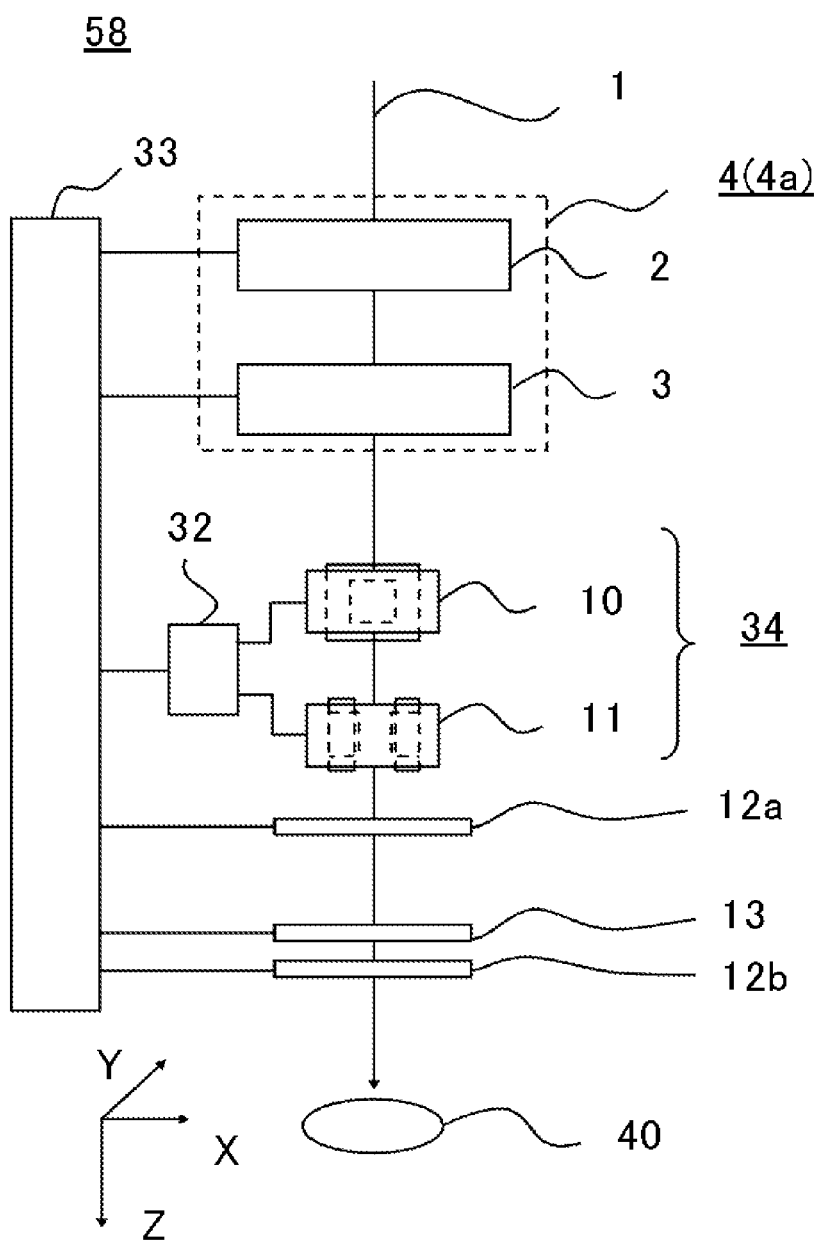
FIG. 1 is a configuration diagram illustrating a particle beam irradiation apparatus according to Embodiment 1 of the present invention.

FIG. 1 is a configuration diagram illustrating a particle beam irradiation apparatus according to Embodiment 1 of the present invention. The particle beam irradiation apparatus 58 is provided with a columnar-irradiation-field generation apparatus 4 that generates a columnar irradiation field by enlarging the BP in the depth direction; X-direction and Y-direction scanning electromagnets 10 and 11 that scan a charged particle beam 1 in the X direction and the Y direction, respectively, which are directions perpendicular to the charged particle beam 1; position monitors 12a and 12b; a dose monitor 13; a scanning electromagnet power source 32; and an irradiation control apparatus 33 that controls the irradiation system of the particle beam irradiation apparatus 58. The X-direction scanning electromagnet 10, the Y-direction scanning electromagnet 11, and the scanning electromagnet power source 32 configure a scanning irradiation system 34 that performs scanning with the charged particle beam 1. The traveling direction of the charged particle beam 1 is the Z direction. The columnar-irradiation-field generation apparatus 4 is provided with an energy changing apparatus 2 that reduces the energy of a charged particle beam at a position before a diseased site 40, which is the irradiation subject, in the traveling direction of the charged particle beam so as to adjust the depth-direction (Z-direction) position (range) of the Bragg peak BP at the diseased site 40; and a depth-direction irradiation field enlargement apparatus 3 that changes the width of the charged particle beam 1 so as to enlarge the Bragg peak BP in the depth direction. The Bragg peak BP whose width in the depth direction of the diseased site 40, i.e., whose irradiation-direction width has been enlarged is referred to as a Spread-Out Bragg Peak SOBP. In this specification, the irradiation-direction width of the Spread-Out Bragg Peak SOBP is referred to as the depth of SOBP.

The X-direction scanning electromagnet 10 is a scanning electromagnet that performs X-direction scanning with the charged particle beam 1; the Y-direction scanning electromagnet is a scanning electromagnet that performs Y-direction scanning with the charged particle beam 1. The position monitors 12a and 12b detect the passing position through which the charged particle beam 1 that has been deflected by the X-direction scanning electromagnet 10 and the Y-direction scanning electromagnet 11 passes. The dose monitor 13 detects the dose of the charged particle beam 1. The irradiation control apparatus 33 controls the columnar irradiation field and the irradiation position on the irradiation subject 40, based on treatment plan data generated by an unillustrated treatment planning apparatus; when the dose measured by the dose monitor 13 reaches the target dose, the charged particle beam is stopped. The scanning electromagnet power source 32 changes setting currents for the X-direction scanning electromagnet 10 and the Y-direction scanning electromagnet 11, based on control inputs (commands), which are outputted from the irradiation control apparatus 33, to the X-direction scanning electromagnet 10 and the Y-direction scanning electromagnet 11.

Figure 2:
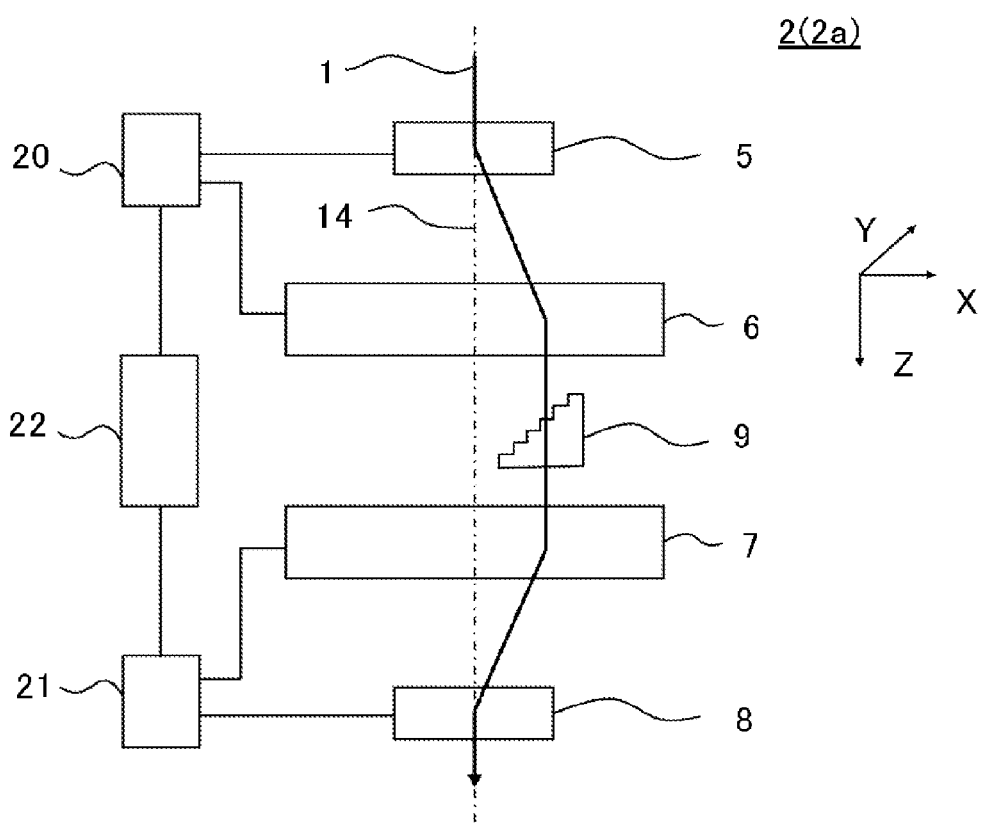
FIG. 2 is a configuration diagram illustrating the energy changing apparatus in FIG. 1.
Figure 3:
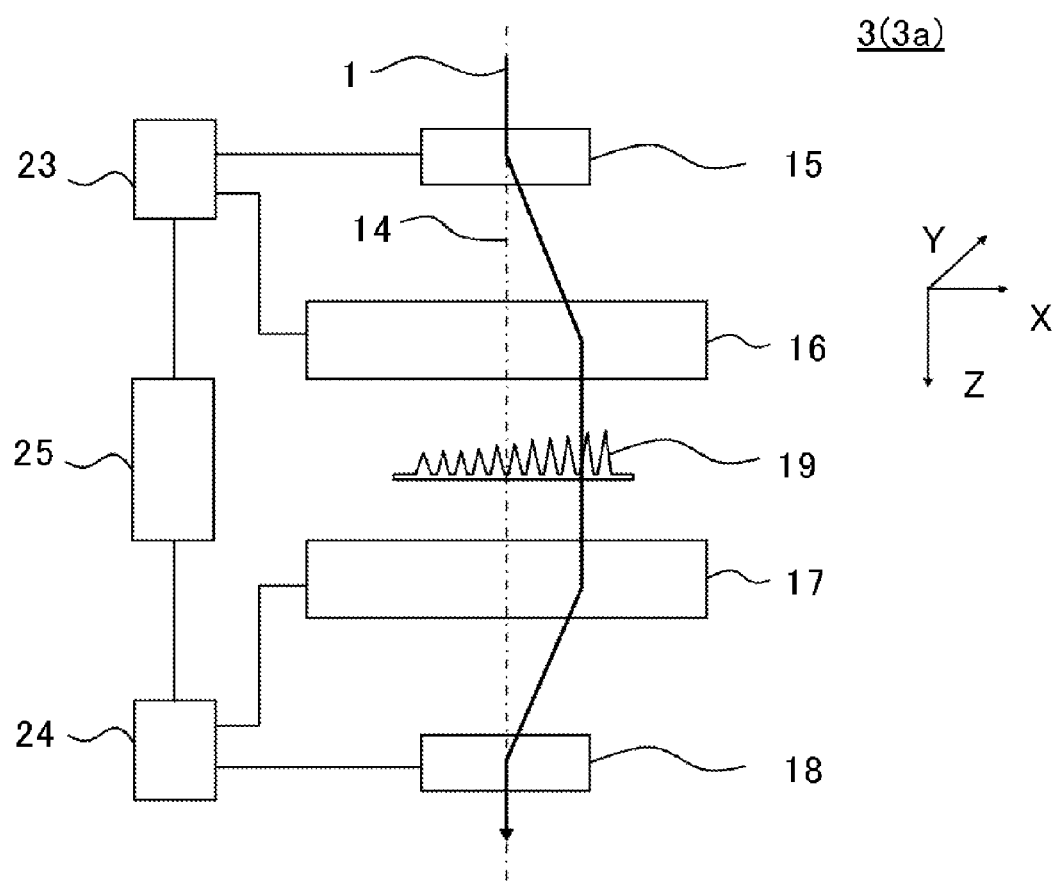
FIG. 3 is a configuration diagram illustrating the depth-direction irradiation field enlargement apparatus in FIG. 1.

FIG. 2 is a configuration diagram illustrating an energy changing apparatus. FIG. 3 is a configuration diagram illustrating a depth-direction irradiation field enlargement apparatus. The energy changing apparatus 2 is provided with a range shifter 9 whose thickness changes in a stepped form in the width direction (X direction); deflection electromagnets 5 and 6 included in a pair of upstream deflection electromagnets that moves the position, of the charged particle beam 1, in the range shifter 9 through which the charged particle beam 1 passes; a first deflection-electromagnet power source 20 that energizes the pair of upstream deflection electromagnets; deflection electromagnets 7 and 8 included in a pair of downstream deflection electromagnets that returns the charged particle beam 1 that has passed through the range shifter 9 onto the original orbit; a second deflection-electromagnet power source 21 that energizes the pair of downstream deflection electromagnets; and a change control apparatus 22 that calculates the amount of movement, of the orbit of the charged particle beam, that is caused by the pair of upstream deflection electromagnets, based on an energy command value inputted from the irradiation control apparatus 33, and transmits an energization current value to the first deflection-electromagnet power source 20. The change control apparatus 22 also controls the second deflection-electromagnet power source 21.

On a beam axis (Z axis) 14, the charged particle beam 1 enters the pair of upstream deflection electromagnets 5 and 6. The orbit of the charged particle beam 1 is moved in the horizontal direction (X direction) on the paper plane of FIG. 2. The deflection electromagnet 5 is to deflect the orbit; the deflection electromagnet 6 is to parallelize the orbit. The deflection electromagnet 5 for changing the orbit deflects the orbit of the incident charged particle beam 1 in such a way that the orbit thereof slants by a predetermined angle θ from the Z axis. The deflection electromagnet 6 for parallelizing the orbit deflects the orbit, which has been slanted from the Z axis by the deflection electromagnet 5 for changing the orbit, to an orbit that is parallel to the Z axis. At the downstream side of the range shifter 9, the deflection electromagnet 7 for deflecting the orbit and the deflection electromagnet 8 for parallelizing the orbit return the charged particle beam 1 onto the beam axis (Z axis) 14. The deflection electromagnet 7 for changing the orbit deflects the orbit of the charged particle beam 1 in such a way that the orbit thereof slants by (360°— the predetermined angle θ) from the Z axis. The deflection electromagnet 8 for parallelizing the orbit deflects the orbit, which has been slanted from the Z axis by the deflection electromagnet 7 for changing the orbit, to an orbit along the Z axis.

The operation of the energy changing apparatus 2 will be explained. Because of the pair of upstream deflection electromagnets 5 and 6, the charged particle beam 1 introduced to the energy changing apparatus 2 travels on an orbit that is parallel to the Z axis and is apart from the Z axis by a predetermined distance toward the X direction. Then, as the charged particle beam 1 passes through a portion, of the range shifter 9, having a predetermined thickness, the energy thereof is reduced by an amount that is proportional to the thickness, and hence becomes desired energy. In such a manner as described above, the charged particle beam 1 whose energy has been changed to a desired level is returned onto the extended line of the original orbit, which was the orbit at a time when the charged particle beam 1 has been launched into the energy changing apparatus 2 by the pair of downstream deflection electromagnets 7 and 8. The energy changing apparatus 2 has an advantage in that, when the energy of a charged particle beam is changed so that the range is changed, no driving sound is produced when the range shifter is driven. In addition, the orbit of the charged particle beam 1 deflected by the pair of downstream deflection electromagnets 7 and 8 is not limited to the one that returns onto the beam axis 14; the orbit may be the one that is parallel to the beam axis 14 and returns toward the beam axis 14, or the orbit may be the one that is not parallel to the beam axis 14 and returns toward the beam axis 14.

FIG. 3 is a configuration diagram illustrating a depth-direction irradiation field enlargement apparatus. The depth-direction irradiation field enlargement apparatus 3 is provided with a ridge filter 19 formed of approximately triangular prisms that are arranged in the width direction (X direction) and whose heights are different from one another, i.e., configured in such a way as to have a plurality of mountains that have different thickness distributions; deflection electromagnets 15 and 16 included in a pair of upstream deflection electromagnets that moves the position, of the charged particle beam 1, in the ridge filter 19 through which the charged particle beam 1 passes; a first deflection-electromagnet power source 23 that energizes the pair of upstream deflection electromagnets; deflection electromagnets 17 and 18 included in a pair of downstream deflection electromagnets that returns the charged particle beam 1 that has passed through the ridge filter 19 onto the original orbit; a second deflection-electromagnet power source 24 that energizes the pair of downstream deflection electromagnets; and a change control apparatus 25 that calculates the amount of movement, of the orbit of the charged particle beam, that is caused by the pair of upstream deflection electromagnets, based on an SOBP command value inputted from the irradiation control apparatus 33, and transmits an energization current value to the first deflection-electromagnet power source 23. The change control apparatus 25 also controls the second deflection-electromagnet power source 24.

On a beam axis (Z axis) 14, the charged particle beam 1 enters the pair of upstream deflection electromagnets 15 and 16. The orbit of the charged particle beam 1 is moved in the horizontal direction (X direction) on the paper plane of FIG. 2. The deflection electromagnet 15 is to deflect the orbit; the deflection electromagnet 16 is to parallelize the orbit. The deflection electromagnet 15 for changing the orbit deflects the orbit of the incident charged particle beam 1 in such a way that the orbit thereof slants by a predetermined angle θ from the Z axis. The deflection electromagnet 16 for parallelizing the orbit deflects the orbit, which has been slanted from the Z axis by the deflection electromagnet 15 for changing the orbit, to an orbit that is parallel to the Z axis. At the downstream side of the ridge filter 19, the deflection electromagnet 17 for deflecting the orbit and the deflection electromagnet 18 for parallelizing the orbit return the charged particle beam 1 onto the beam axis (Z axis) 14. The deflection electromagnet 17 for changing the orbit deflects the orbit of the charged particle beam 1 in such a way that the orbit thereof slants by (360°— the predetermined angle θ) from the Z axis. The deflection electromagnet 18 for parallelizing the orbit deflects the orbit, which has been slanted from the Z axis by the deflection electromagnet 17 for changing the orbit, to an orbit along the Z axis.

The operation of the depth-direction irradiation field enlargement apparatus 3 will be explained. Because of the pair of upstream deflection electromagnets 15 and 16, the charged particle beam 1 introduced to the depth-direction irradiation field enlargement apparatus 3 travels on an orbit that is parallel to the Z axis and is apart from the Z axis by a predetermined distance toward the X direction. Then, as the charged particle beam 1 passes through a portion, of the ridge filter 19, having a predetermined thickness distribution, the energy thereof is reduced by an amount that is proportional to the thickness; as a result, there is produced a particle beam in which many kinds of energies whose intensities are different from one another are mixed. The depth of SOBP can be changed in accordance with the height of the ridge filter 19 through which the charged particle beam 1 passes. In such a manner as described above, the charged particle beam 1 whose width has been changed to a desired SOBP depth is returned onto the extended line of the original orbit, which was the orbit at a time when the charged particle beam 1 has been launched into the depth-direction irradiation field enlargement apparatus 3 by the pair of downstream deflection electromagnets 17 and 18. The depth-direction irradiation field enlargement apparatus 3 has an advantage in that, when the depth of SOBP is changed, no driving sound is produced when the ridge filter is driven. In addition, the orbit of the charged particle beam 1 deflected by the pair of downstream deflection electromagnets 17 and 18 is not limited to the one that returns onto the beam axis 14; the orbit may be the one that is parallel to the beam axis 14 and returns toward the beam axis 14, or the orbit may be the one that is not parallel to the beam axis 14 and returns toward the beam axis 14.

By mounting the particle beam irradiation apparatus 58 on a rotating gantry, the irradiation system of the particle beam irradiation apparatus 58 can freely be rotated around a patient platform, whereby there can be performed irradiation onto the diseased site 40 from many directions. The rotating gantry rotates the irradiation system of the particle beam irradiation apparatus 58 so as to rotate the irradiation direction. That is to say, multi-port irradiation can be performed in this manner. By use of the ridge filter 19 in the particle beam irradiation apparatus 58, the irradiation field is more enlarged in the Z direction than in the X direction and the Y direction; thus, a beam with a columnar dose distribution (refer to FIGS. 5A through 5D) can be irradiated onto the diseased site 40.

Next, a method of performing IMRT through columnar scanning irradiation will be explained. FIG. 4 is a flowchart representing a method of generating a treatment plan utilized in a particle beam irradiation apparatus according to the present invention; each of FIGS. 5A through 5D is a view for explaining the step ST1 in FIG. 4; each of FIGS. 6A through 6C is a schematic diagram for obtaining the initial state in an optimum calculation for a treatment plan. FIGS. 5A through 5D and FIGS. 6A through 6C are examples in which irradiation is performed with a four-port (every 90°) irradiation apparatus. The treatment planning apparatus for generating a treatment plan is provided with an irradiation field arranging unit that arranges columnar irradiation fields in accordance with the distal form of the diseased site (irradiation subject) 40 onto which the charged particle beam 1 is irradiated, and arranges columnar irradiation fields in such a way that the columnar irradiation fields cover the inside of the diseased site (irradiation subject) 40; and an optimization calculation unit that adjusts the arrangement of the columnar irradiation fields in such a way that the irradiation dose onto the diseased site (irradiation subject) 40 falls within a predetermined range, regarding, as the initial state, the state in which the columnar irradiation fields are arranged by the irradiation field arranging unit. A treatment plan includes the operation conditions for the particle beam irradiation apparatus 58 and the rotating gantry; the particle beam irradiation apparatus 58 and the rotating gantry integrally operate based on the treatment plan.

Figure 5A:
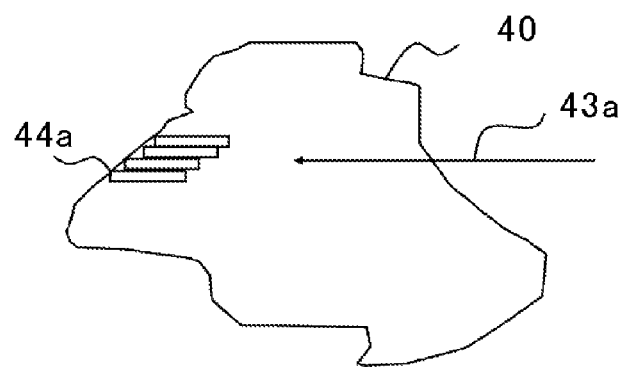
Figure 5B:
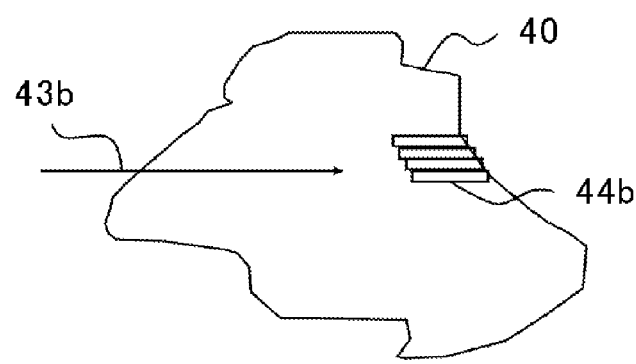
Figure 5C:
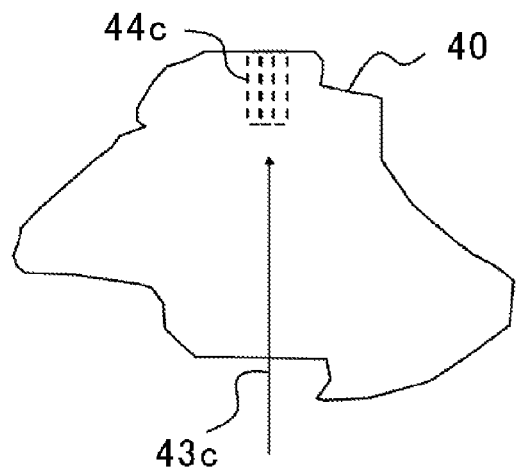
Figure 5D:
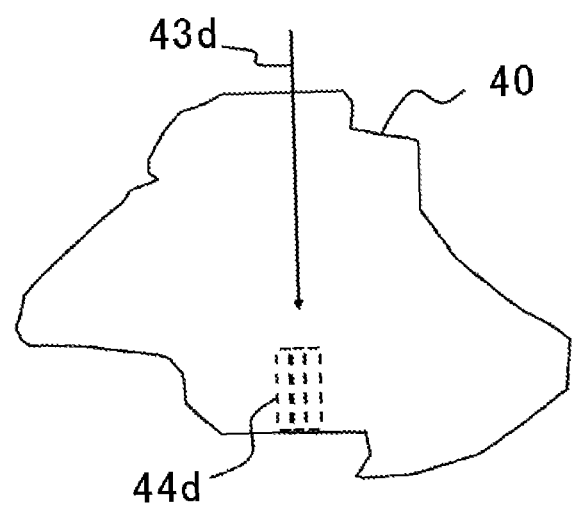

At first, as illustrated in FIGS. 5A through 5D, columnar irradiation fields 44*a*, 44*b*, 44*c*, and 44*d* are arranged in accordance with the distal form of the diseased site 40 (the step ST1). This action is implemented for each port (for each radiation direction). In this situation, the columnar irradiation fields may overlap with one another. Portions where the columnar irradiation fields overlap with one another will be explained later. FIG. 5A is an example of the case where the columnar irradiation fields 44*a* are arranged in accordance with the distal form of the diseased site 40 at a time when irradiation is performed from an irradiation direction 43*a*; FIG. 5B illustrates the columnar irradiation fields 44*b* at a time when irradiation is performed from an irradiation direction 43*b*; FIG. 5C illustrates the columnar irradiation fields 44*c* at a time when irradiation is performed from an irradiation direction 43*c*; FIG. 5D illustrates the columnar irradiation fields 44*d* at a time when irradiation is performed from an irradiation direction 43*d*. FIG. 6A illustrates an example of irradiation field arrangement at a time when all irradiations with the respective ports (radiation directions) have been completed.

When all irradiations with respective ports (radiation directions) have been completed, it is determined whether or not there exists any remaining irradiation-subject region (the step ST2). In the case where there exists no remaining irradiation-subject region, the step ST2 is followed by the step ST5. In the case where there exists a remaining irradiation-subject region, the second-round arrangement work is performed in the remaining irradiation-subject region in such a way that the arrangement matches the distal form of the remaining irradiation subject (the step ST3). As illustrated in FIG. 6B, in the case where irradiation is performed from the irradiation direction 43*c*, the columnar irradiation fields 45*c* are arranged. In this situation, the depth of SOBP in the second-round columnar irradiation field may be different from that in the first-round columnar irradiation field. FIG. 6C illustrates an example of irradiation field arrangement at a time when all irradiations with the respective ports (radiation directions) have been completed. In FIG. 6C, in the case where irradiation is performed from the irradiation direction 43*a*, the columnar irradiation fields 45*a* are arranged; in the case where irradiation is performed from the irradiation direction 43*b*, the columnar irradiation fields 45*b* are arranged; in the case where irradiation is performed from the irradiation direction 43*d*, the columnar irradiation fields 45*d* are arranged.

When all irradiations with respective ports (radiation directions) have been completed in the second round, it is determined whether or not there exists any remaining irradiation-subject region (the step ST4). In the case where there exists a remaining irradiation-subject region, the step ST4 is followed by the step ST3; this flow is repeated so that the columnar irradiation fields cover the whole diseased site. In the case where there exists no remaining irradiation-subject region, the step ST4 is followed by the step ST5.

In the step ST5, optimization calculation is performed, regarding, as the initial value, the irradiation plan where the columnar irradiation fields have been arranged. After the optimization calculation has been completed, evaluation is performed by use of an evaluation function (the step ST6). It is determined whether or not the value of the evaluation function is allowable in terms of the clinical practice; in the case where it is determined that the value of the evaluation function is not allowable, the step ST6 is followed by the step ST5, and then the optimization calculation is implemented. In the case where the value of the evaluation function is within an allowable range in terms of the clinical practice, the flow is ended.

In the treatment-plan optimization work represented in the steps ST5 and ST6, in order to prevent overdosing (excess dose), the arrangement of the columnar irradiation fields is adjusted so that the irradiation dose onto the diseased site 40 falls within a predetermined range. In the foregoing portion where the columnar irradiation fields overlap with one another, overdosing (excess dose) is caused; therefore, in the optimization work, the arrangement of the columnar irradiation fields is changed in such a way that the portions where the columnar irradiation fields overlap with one another are eliminated or reduced.

The work in the steps ST1 through ST4 is performed first by the irradiation field arranging unit of the treatment planning apparatus. Next, the treatment planning apparatus will be explained. The detail of a treatment planning apparatus is described in "the Radiation Therapy System Operating Manual for Medical Safety" (by Kozo Kumagai, Publishing Company of JART). A treatment planning apparatus has a comprehensive role; in brief, it can be referred to as a treatment simulator. One of the roles of a treatment planning apparatus is optimization calculation. The optimization work for a treatment plan represented in the steps ST5 and ST6 is performed in the optimization calculation unit of the treatment planning apparatus. The optimization calculation is utilized in searching the optimum beam intensity in an IMRT inverse treatment plan (inverse planning).

According to the foregoing operation manual, as the optimization calculation method, there have been tried following methods to date. The methods are the filtered back projection method which was utilized in earlier years in performing IMRT optimization calculation; pseudo annealing, genetic algorithm, and random searching technology that are classified into a probabilistic method; and the gradient method which is classified into the deterministic method that has recently been installed in many treatment planning apparatuses.

Although the calculation in the gradient method is high-speed, it has a nature that, once the calculation is trapped in a local minimum (the smallest possible quantity), it cannot get out of the trap. However, at present, the gradient method has been adopted in many treatment planning apparatuses that implement clinic practice IMRT treatment plans.

In the gradient method, in order to prevent the situation where the calculation is trapped in another minimum value which is different from the optimum value to be obtained, it is effective to use the gradient method combined with the genetic algorithm or the random searching technology. In addition, it is empirically known that it is desirable that the initial value (a value initially given as a candidate of the solution) in the optimization calculation is close to the optimum solution to be obtained.

Thus, in the present invention, an irradiation plan generated in the steps ST1 through ST4 is utilized as the initial value in the optimization calculation. Because, compared with conventional IMRT, its irradiation flexibility in the depth direction is made high for the purpose of matching the distal form of a diseased site, the irradiation plan generated in the steps ST1 through ST4 is sufficiently close to the optimum irradiation.

In the optimization calculation, there is calculated a solution that certainly minimizes a given evaluation function. In the case of a treatment planning apparatus, as represented in the foregoing operation manual, the evaluation function, which is the reference for physical optimization, is given as follows.

$$F_T(\vec{b}) = \sum_{i=1}^{N} \left( u[D_{min} - d_i(\vec{b})]_+^2 = w[d_i(\vec{b}) - D_{max}]_+^2 \right) \quad (1)$$

where $D_{min}$ and $D_{max}$ are specified dose limits. The character "u" is a weight coefficient for $D_{min}$; "w" is a weight coefficient for $D_{max}$. The character "b" (although indicated with an arrow in the equation (1), indicated without the arrow in the description. Hereinafter, the same applies in the explanation for the equation (1).) is a function of the intensity of a beamlet; $d_i(b)$ is the dose in a voxel "i" represented by the function "b" of the intensity of a beamlet. $[x]_+$ is x, in the case where x>0, and $[x]_+$ is "0" in other cases. N is the maximum number of voxels.

As described above, optimization calculation is implemented in the treatment planning apparatus; therefore, for example, even though, with an initial value, columnar irradiation fields overlap with one another and hence overdosing (excess dose) is caused, the dose is adjusted in an obtained treatment plan.

Because being configured as described above, the treatment planning apparatus according to Embodiment 1 can raise the irradiation flexibility in the depth direction, without utilizing a bolus; therefore, there can be solved the problem of excess irradiation in IMRT by a particle beam therapy system.

The advantage of irradiating a beam having a columnar dose distribution will be explained. Originally, in a conventional particle beam therapy system in which it is assumed that irradiation is performed from one direction, the dose distribution in the irradiation system is formed in the following manner. As an example, the Wobbler method will be explained; a Wobbler electromagnet and a scatterer evenly enlarge the irradiation field in the X and Y directions, and based on the XY-plane sectional shape (or the shape projected onto the XY plane, for example,) of a diseased site, the irradiation field is limited by an MLC. The irradiation field is enlarged by a ridge filter in the Z direction and is limited by a bolus in such a way as to coincide with the distal form (the deepest-layer form) of the diseased site.

As described above, in the multi-port irradiation by a particle beam therapy system, it is required to utilize a plurality of boluses; therefore, machining of the bolus requires many labor hours and costs. Moreover, the bolus cannot be dynamically deformed; thus, the multi-port irradiation cannot be applied to IMAT. If, in the multi-port irradiation by a particle beam therapy system, the irradiation field can be controlled, as by a bolus, in such a way as to coincide with the distal form (the deepest-layer form) of a diseased site without utilizing a bolus, there can be solved the problem that machining of the bolus requires many labor hours and costs; therefore, the multi-port irradiation can be applied to IMAT, whereby the problem of excess irradiation in IMRT can be solved, i.e., the unnecessary irradiation onto normal tissues can considerably be reduced. That led to the present invention in which a beam having a columnar dose distribution is irradiated. In the present invention, one of the greatest effects of irradiating a beam having a columnar dose distribution is that the irradiation field can be limited in such a way as to coincide with the distal form (the deepest-layer form) of the diseased site 40 without utilizing a bolus and hence the unnecessary irradiation onto normal tissues can considerably be reduced.

Another one of the greatest effect, in the present invention, of irradiating a beam having a columnar dose distribution is that an irradiation field can be formed without implementing the intensity modulation which is adopted in a radiation therapy system utilizing an X-ray or the like. Here, for the simplicity, the principle of the intensity modulation may be explained as follows. Irradiation fields having a weak dose distribution are irradiated from many directions so that the irradiation fields overlap with one another; the portion where the doses eventually overlap most with one another obtains the dose distribution, as the irradiation field that provides an treatment effect.

In the present invention, as illustrated in FIGS. 6A through 6C, an irradiation field can be formed by combining columnar doses. Additionally, there may be performed irradiation with irradiation fields overlapping with one another in the present invention, as well. It is not allowed that the irradiation dose becomes an underdose (insufficient dose) or an overdose (excess dose) in any portion of a diseased site; however, the dose that is allowable in terms of a clinical practice has a width. An irradiation plan is made by use of a treatment planning apparatus in such a way that the final dose distribution is allowable in each portion of the diseased site. Unlike a conventional radiation therapy system utilizing an X-ray or the like, it is not required to perform intensity modulation of the irradiation field in such a way that it coincides with the distal form of the diseased site; therefore, the treatment planning apparatus is not required to perform calculation for optimizing the intensity modulation. That is to say, there can be solved the conventional problem that it takes a long time to make a treatment plan. Moreover, compared with irradiation of a beam having a spot-like distribution, irradiation of a beam having a columnar dose distribution has an advantage in that the irradiation time is shortened.

In the case where multi-port irradiation can be performed in a particle beam therapy system utilizing the treatment planning apparatus according to Embodiment 1, there exist a number of advantages; the following two are the major advantages. The first one is that, in the case where irradiation is performed onto the same diseased site, multi-port irradiation makes wider the body surface area through which a particle beam passes; thus, the damage to the body surface area, which includes normal tissues, can be reduced. The second one is that irradiation can be prevented from being preformed onto a risk site (such as a spinal cord, an eyeball or the like), onto which a particle beam should not be irradiated.

As described above, the particle beam irradiation apparatus 58 according to Embodiment 1 is provided with the scanning irradiation system 34 that performs scanning with the charged particle beam 1, and is mounted in a rotating gantry that rotates the irradiation direction of the charged particle beam 1; because the particle beam irradiation apparatus 58 includes the columnar-irradiation-field generation apparatus 4 that enlarges the Bragg peak of the charged particle beam 1 so as to generate a columnar irradiation field, there can be irradiated a columnar irradiation field obtained by enlarging the Bragg peak of a charged particle beam, at the depth in accordance with the distal form of an irradiation subject, in such a way that the columnar field is generated; therefore, there can be raised the irradiation flexibility in the depth direction, without utilizing a bolus. As a result, there can be solved the problem of excess irradiation in IMRT by a particle beam therapy system.

Embodiment 2

FIG. 7 is a configuration diagram illustrating an energy changing apparatus according to Embodiment 2 of the present invention. An energy changing apparatus according to Embodiment is different from the energy changing apparatus 2a according to Embodiment 1 in that the energy of a charged particle beam 1 is reduced to a desired energy by use of a plurality of absorbers 26a, 26b, 26c, and 26d so that there is adjusted the depth-direction (Z-direction) position (range) of the Bragg peak BP at a diseased site 40, which is an irradiation subject.

An energy changing apparatus 2b includes a plurality of absorbers 26a, 26b, 26c, and 26d that are driven by driving devices 27a, 27b, 27c, and 27d. The absorbers 26a, 26b, 26c, and 26d are different in thickness from one another. The thickness of the overall absorber can be changed by combining the respective thicknesses of the absorbers 26a, 26b, 26c, and 26d. A change control apparatus 22 controls the driving devices 27a, 27b, 27c, and 27d so that the charged particle beam 1 passes or does not pass through the absorbers 26a, 26b, 26c, and 26d that correspond to the driving devices 27a, 27b, 27c, and 27d, respectively. The energy of the charged particle beam 1 is reduced by an amount that is proportional to the thickness of the absorber through which the charged particle beam 1 passes, and hence becomes desired energy.

As is the case with Embodiment 1, the particle beam irradiation apparatus (refer to FIG. 1) having the energy changing apparatus 2b according to Embodiment 2 can enlarge the Bragg peak BP in the depth direction so as to generate a columnar irradiation field. In the energy changing apparatus 2b according to Embodiment 2, it is not required to deflect the charged particle beam 1; therefore, compared with the energy changing apparatus 2a according to Embodiment 1, the deflection electromagnets 5 through 8 can be removed, whereby the length L1 of the apparatus in the irradiation direction (Z direction) of the charged particle beam 1 can be shortened. Because the length L1 of the apparatus can be shortened, the energy changing apparatus can be made compact. The length L1 of the apparatus in FIG. 2 is the length from the upstream end of the deflection electromagnet 5 to the downstream end of the deflection electromagnet 8.

In the particle beam irradiation apparatus (refer to FIG. 1) having the energy changing apparatus 2b according to Embodiment 2, multi-port irradiation can be implemented based on a treatment plan corresponding to the treatment plan generated by the treatment planning apparatus described in Embodiment 1; therefore, as is the case with Embodiment 1, the irradiation flexibility in the depth direction can be raised, without utilizing a bolus. As a result, there can be solved the problem of excess irradiation in IMRT by a particle beam therapy system.

Embodiment 3

FIG. 8 is a configuration diagram illustrating a depth-direction irradiation field enlargement apparatus according to Embodiment 3 of the present invention. A depth-direction irradiation field enlargement apparatus 3b according to Embodiment 3 is different from the depth-direction irradiation field enlargement apparatus 3a according to Embodiment 1 in that the energy of a charged particle beam is formed of many kinds of energy levels that are mixed by use of a plurality of ridge filters 28a, 28b, 28c, and 28d, i.e., the energy width of the charged particle beam 1 is changed so that the Bragg peak BP is enlarged in the depth direction.

The depth-direction irradiation field enlargement apparatus 3b includes a plurality of ridge filters 28a, 28b, 28c, and 28d that are driven by driving devices 29a, 29b, 29c, and 29d. The ridge filters 28a, 28b, 28c, and 28d are different in thickness from one another. The thickness of the overall ridge filter can be changed by combining the respective thicknesses of the ridge filters 28a, 28b, 28c, and 28d. A change control apparatus 25 controls the driving devices 29a, 29b, 29c, and 29d so that the charged particle beam 1 passes or does not pass through the ridge filters 28a, 28b, 28c, and 28d that correspond to the driving devices 29a, 29b, 29c, and 29d, respectively. The energy range of the charged particle beam 1 is widened by an amount that is proportional to the thickness of the ridge filter through which the charged particle beam 1 passes, and hence becomes a desired depth of SOBP.

As is the case with Embodiment 1, the particle beam irradiation apparatus (refer to FIG. 1) having the depth-direction irradiation field enlargement apparatus 3b according to Embodiment 3 can enlarge the Bragg peak BP in the depth direction so as to generate a columnar irradiation field. In the depth-direction irradiation field enlargement apparatus 3b according to Embodiment 3, it is not required to deflect the charged particle beam 1; therefore, compared with the energy changing apparatus 2a according to Embodiment 1, the deflection electromagnets 15 through 18 can be removed, whereby the length L2 of the apparatus in the irradiation direction (Z direction) of the charged particle beam 1 can be shortened. Because the length L2 of the apparatus can be shortened, the energy changing apparatus can be made compact. The length L2 of the apparatus in FIG. 3 is the length from the upstream end of the deflection electromagnet 15 to the downstream end of the deflection electromagnet 18.

In the particle beam irradiation apparatus (refer to FIG. 1) having the depth-direction irradiation field enlargement apparatus 3b according to Embodiment 3, multi-port irradiation can be implemented based on a treatment plan corresponding to the treatment plan generated by the treatment planning apparatus described in Embodiment 1; therefore, as is the case with Embodiment 1, the irradiation flexibility in the depth direction can be raised, without utilizing a bolus. As a result, there can be solved the problem of excess irradiation in IMRT by a particle beam therapy system.

Embodiment 4

FIG. 9 is a configuration diagram illustrating a columnar-irradiation-field generation apparatus according to Embodiment 4 of the present invention. A columnar-irradiation-field generation apparatus according to Embodiment 4 is different from the columnar-irradiation-field generation apparatus 4a according to Embodiment 1 in that the energy changing apparatus 2a and the depth-direction irradiation field enlargement apparatus 3a are integrated.

The columnar-irradiation-field generation apparatus 4b is provided with range shifters 9a and 9b; ridge filters 19a and 19b; deflection electromagnets 5 and 6 included in a pair of upstream deflection electromagnets that moves the position, of the charged particle beam 1, in the range shifters 9a and 9b and the ridge filters 19a and 19b through which the charged particle beam 1 passes; a first deflection-electromagnet power source 20 that energizes the pair of upstream deflection electromagnets; deflection electromagnets 7 and 8 included in a pair of downstream deflection electromagnets that returns the charged particle beam 1 that has passed through the range shifters 9a and 9b and the ridge filters 19a and 19b onto the original orbit; a second deflection-electromagnet power source 21 that energizes the pair of downstream deflection electromagnets; and a change control apparatus 22 that calculates the amount of movement, of the orbit of the charged particle beam, that is caused by the pair of upstream deflection electromagnets, based on an energy command value inputted from the irradiation control apparatus 33, and transmits an energization current value to the first deflection-electromagnet power source 20. The change control apparatus 22 also controls the second deflection-electromagnet power source 21. The operations of the apparatuses are the same as those in Embodiment 1; thus, explanations therefor will not be repeated.

The range shifters 9a and 9b are formed in the same shape and formed of the same material; the ridge filter 19a is formed of the first group of approximately triangular prisms and the ridge filter 19b is formed of the second group of approximately triangular prisms; the height of the first group of approximately triangular prisms is different from the height of the second group of approximately triangular prisms. The height of the second group of approximately triangular prisms of the ridge filter 19b is higher than the height of the first group of approximately triangular prisms of the ridge filter 19a; therefore, the depth of SOBP of the charged particle beam 1 in the case where the charged particle beam 1 passes through the ridge filter 19b can be wider than the depth of SOBP of the charged particle beam 1 in the case where the charged particle beam 1 passes through the ridge filter 19a.

The columnar-irradiation-field generation apparatus 4b according to Embodiment 4 changes the energy of the charged particle beam 1 to desired energy, through two kinds of SOBP depths; thus, two kinds of columnar irradiation fields can have desired ranges. There are not provided the pair of upstream electromagnets and the pair of downstream deflection electromagnets for each of the set of the range filter 9a and the ridge filter 19a and the set of the range filter 9b and the ridge filter 19b, but there is provided only one set of the pair of upstream electromagnets and the pair of downstream deflection electromagnets; therefore, compared with the columnar-irradiation-field generation apparatus 4a according to Embodiment 1, the length of the apparatus in the irradiation direction (Z direction) of the charged particle beam 1 can be shortened. By use of the pair of upstream deflection electromagnets and the pair of downstream deflection electromagnets, the energy of the charged particle beam 1 is changed to desired energy through two kinds of SOBP depths; thus, there exists an advantage that, when the width and the range of SOBP are changed, there is produced no driving sound caused due to driving of the range filter or the ridge filter. In order to line up many kinds (more than two) of SOBP depths, it is only necessary to arrange the range filters 9 and the ridge filters 19, the number of each of which corresponds to the number of the kinds of SOBPs.

In the particle beam irradiation apparatus (refer to FIG. 1) having the columnar-irradiation-field generation apparatus 4b according to Embodiment 4, multi-port irradiation can be implemented based on a treatment plan corresponding to the treatment plan generated by the treatment planning apparatus described in Embodiment 1; therefore, as is the case with Embodiment 1, the irradiation flexibility in the depth direction can be raised, without utilizing a bolus. As a result, there can be solved the problem of excess irradiation in IMRT by a particle beam therapy system.

Embodiment 5

In each of Embodiments 1 through 4, it has been explained that the Z-direction enlargement of an irradiation field, i.e., an SOBP is realized by means of the ridge filter 19 (28). As Embodiment 5, there will be explained an embodiment in which in order to enlarge an irradiation field more to the Z direction than either to the X direction or the Y direction, a range modulation wheel RMW (Range Modulation Wheel) is utilized.

An RWM, which is an apparatus utilized in an apparatus included in an irradiation system, i.e., utilized in a particle beam irradiation apparatus, is to create an SOBP by enlarging an irradiation field in the traveling direction of a beam. In some cases, an RMW is utilized in a broad beam irradiation method, such as the double scatterer method or the Wobbler method, in which the irradiation field of a beam is temporarily enlarged and then is limited through a collimator or a bolus. Japanese Patent Application Laid-Open No. 2007-222433 discloses an example where an RMW is utilized in the double scatterer method. An RMW according to Embodiment 5 of the present invention will be explained with reference to FIGS. 10 and 11.

FIG. 10 is an external view illustrating an RMW according to Embodiment 5 of the present invention; FIG. 11 is a configuration diagram illustrating a depth-direction irradiation field enlargement apparatus according to Embodiment 5 of the present invention. An RMW 35 is configured in such a way that there are arranged a plurality of wedge-shaped energy absorbers (blades) which are each configured with a plurality of pedestals, the respective axis-direction thicknesses of which stepwise increase or decrease. In the example illustrated in FIG. 10, the RMW 35 has three blades 37a, 37b, and 37c. The blades 37a, 37b, and 37c each have six pedestals 36a, 36b, 36c, 36d, 36e, and 36f and a shape in which the respective axis-direction thicknesses of the pedestals stepwise decrease in the clockwise circumferential direction, i.e., in the direction from the pedestal 36a to the pedestal 36f. By utilizing the pedestal 36, RMW 35 is represented in the following manner. The RMW 35 has energy absorbers 37 in each of which a plurality of pedestals 36a through 36f, the respective axis-direction thicknesses of which are stepwise different from one another, are arranged in the circumferential direction; when a charged particle beam 1 passes through the plurality of pedestals 36a through 36f, the energy thereof varies. The blades 37a, 37b, and 37c are arranged in angle ranges 0° to 120°, 120° to 240°, and 240° to 360°) (0°, respectively. The six pedestals 36a, 36b, 36c, 36d, 36e, and 36f are arranged in such a way as to be spaced 20° apart from one another. The RMW 35 is disposed in the beam path in a particle beam irradiation apparatus and rotates on a plane perpendicular to the beam path. For example, the RMW 35 is disposed at the upstream side of the scanning irradiation system 34 illustrated in FIG. 1.

There will be explained a principle in which an SOBP is formed by the RMW 35. For example, in the case where while the RMW 35 rotates, the charged particle beam 1 passes through a thin portion of the blade (e.g., the pedestal 36f), the attenuation of the beam energy is small and hence a Bragg peak BP is produced in a deep part of a body. In the case where the charged particle beam 1 passes through a thick portion of the blade (e.g., the pedestal 36a), the attenuation of the beam energy is large and hence a Bragg peak BP is produced in a shallow part of a body. Because due to the rotation (circulation) of the RMW 35, the position of the Bragg peak BP fluctuates periodically, there can be obtained, in view of time integration, a flat dose distribution (SOBP) that spreads from a shallow part, which is near to the body surface, to a deep part of a body.

By selecting two or more neighboring pedestals and making the charged particle beam 1 pass through only the selected pedestals, two or more depths of SOBP can be formed. For example, the depth of SOBP at a time when the pedestals 36e and 36f are selected is referred to as "SOBP depth 1". As is the case with SOBP depth 1, the depths of SOBP at times when the pedestals 36d through 36f, 36c through 36f, 36b through 36f, and 36a through 36f are selected are referred to as "SOBP depth 2", "SOBP depth 3", "SOBP depth 4", and "SOBP depth 5", respectively. In the example utilizing the RMW 35 illustrated in FIG. 10, when the selection is performed in such a way that the pedestal 36f is always included, five depths of SOBP can be formed and based on these depths of SOBP, the depth of SOBP can freely be selected and changed.

The RMW 35 according to the present invention is utilized to enlarge a Bragg peak BP more in the depth direction than a conventional spot so that the columnar irradiation fields 44 and (refer to FIG. 6) are created. A particle beam irradiation apparatus according to Embodiment 5 has a configuration illustrated in FIG. 1. In other words, naming from the upstream side of the charged particle beam 1, the particle beam irradiation apparatus according to Embodiment 5 is provided with a columnar-irradiation-field generation apparatus 4, a pair of scanning electromagnets 10 and 11, position monitors 12a and 12b, and a dose monitor 13; the particle beam irradiation apparatus is controlled by an irradiation control apparatus 33. In this regard, however, the columnar-irradiation-field generation apparatus 4 is a depth-direction irradiation field enlargement apparatus 3 (3c) provided with the RMW 35.

The columnar-irradiation-field generation apparatus 4 according to Embodiment 5 has an energy changing apparatus 2 and the depth-direction irradiation field enlargement apparatus 3 (3c). The depth-direction irradiation field enlargement apparatus 3c will be explained with reference to FIG. 11. The depth-direction irradiation field enlargement apparatus 3c has the RMW 35, a rotation axle 64 for rotating the RMW 35, a motor (rotation drive device) 62 that drives the rotation axle 64 for rotating the RMW 35, an angle sensor 61 for detecting the rotation angle of the rotation axle 64, and an irradiation-field enlargement control apparatus 65 that transmits to the irradiation control apparatus 33 a control signal Sig1 for controlling the emission start and the emission stop of the charged particle beam 1. The motor 62 and the rotation axle 64 that are arranged at positions that do not interfere with the charged particle beam 1 are coupled with each other, for example, by means of bevel gears (coupling devices) 63a and 63b. The irradiation-field enlargement control apparatus 65 controls the rotation of the motor 62. In this embodiment, the irradiation-field enlargement control apparatus 65 controls the rotation of the motor 62 in such a way that the RMW 35 keeps rotating at a predetermined constant speed. The RMW 35, the rotation axle 64, the motor 62, the bevel gears (coupling devices) 63a and 63b, and the angle sensor 61 configure an RMW apparatus 66. The RMW apparatus 66 changes the position of the RMW 35, through which the charged particle beam 1 passes, so as to vary the energy of the charged particle beam 1. The irradiation-field enlargement control apparatus 65 performs control in such a way that the charged particle beam 1 passes through two or more pedestals 36a through 36f.

The operation of the depth-direction irradiation field enlargement apparatus 3c will be explained. There will be explained a case where the depth of SOBP, in a certain columnar irradiation field 44, that is specified in a treatment plan is SOBP depth 4, for example. SOBP depth 4 is formed when the charged particle beam 1 passes through the angles corresponding to the pedestals 36b through 36f. The charged particle beam 1 is irradiated in the columnar irradiation field 44 until the dose specified in a treatment plan is satisfied (the dose reaches a target dose). The charged particle beam 1 passes at least once through the blade 37 in which the pedestals 36a through 36f are provided, by the time the dose of the columnar irradiation field is satisfied. The RMW 35 is controlled by the motor 62 in such a way as to rotate in a direction indicated as a rotation direction 68.

The emission of the charged particle beam 1 for the columnar irradiation field 44 is started at a time when the angle sensor 61 detects an angle-area starting angle 20° (140°, 260°), in the angle 20° to 40° corresponding to the pedestal 36b, which is an emission starting angle. When the angle sensor 61 detects the emission starting angle, the irradiation-field enlargement control apparatus 65 outputs the control signal Sig1 (e.g., a first voltage level). In response to the control signal Sig1, the irradiation control apparatus 33 issues an emission start instruction that the emission apparatus of the accelerator emits the charged particle beam 1 to the particle beam irradiation apparatus 58. In response to the emission start instruction, the emission apparatus of the accelerator emits the charged particle beam 1 to the particle beam irradiation apparatus 58 (beam emission procedure). Next, when the angle sensor 61 detects an emission stop angle (120°, 240°, 360°(0°)), the irradiation-field enlargement control apparatus 65 stops the control signal Sig1 (e.g., the level of the control signal Sig1 is changed to a second voltage level). In response to the stop of the control signal Sig1, the irradiation control apparatus 33 issues an emission stop instruction that the emission apparatus of the accelerator stops the emission of the charged particle beam 1 to the particle beam irradiation apparatus 58. In response to the emission stop instruction, the emission apparatus of the accelerator stops the emission of the charged particle beam 1 to the particle beam irradiation apparatus 58 (beam stop procedure).

Next, the beam emission procedure and the beam stop procedure are repeated also in the following blade 37 until the dose monitor detects the fact that the dose has been satisfied. When the dose monitor detects the fact that the dose has been satisfied, in response to the satisfaction of the dose, the irradiation control apparatus 33 issues an emission stop instruction that the emission apparatus of the accelerator stops the emission of the charged particle beam 1 to the particle beam irradiation apparatus 58. In response to the emission stop instruction, the emission apparatus of the accelerator stops the emission of the charged particle beam 1 to the particle beam irradiation apparatus 58 (columnar irradiation field stop procedure). After that, the process moves to a procedure in which the next columnar irradiation field is formed. The procedure for forming a columnar irradiation field includes the beam emission procedure, the beam stop procedure, and the columnar irradiation field stop procedure.

The particle beam irradiation apparatus 58 having the depth-direction irradiation field enlargement apparatus 3c according to Embodiment 5 can perform irradiation in such a way as to generate a columnar irradiation field, which is obtained by enlarging the Bragg peak of a charged particle beam, at the depth corresponding to the distal form of an irradiation subject, and there can be raised the irradiation flexibility in the depth direction, without utilizing a bolus; therefore, there can be solved the problem of excess irradiation in IMRT by a particle beam therapy system.

The RMW 35 demonstrates an advantageous effect that is not found in a ridge filter. AS illustrated in FIG. 6, in some cases, it is required that in the second-round columnar irradiation field 45, the depth of SOBP is different from the depth of SOBP in the first-round columnar irradiation field 44, depending on the shape of the diseased site 40. In the case where the depth of SOBP is changed by means of a ridge filter, it is required to prepare a plurality of ridge filters, as illustrated in FIGS. 8 and 9. In contrast, in the case of an RMW, the emission start and the emission stop of the charged particle beam 1 are controlled based on the rotation angle of the RMW 35, so that the depth of SOBP can freely be changed. That is to say, as described above, by synchronizing the rotation of the RMW 35 with the timing of beam emission, the depth of SOBP can freely be controlled by means of a single RMW 35. As a result, in the case where a plurality of depths of SOBP is formed, the configuration of the columnar-irradiation-field generation apparatus 4 can be simplified.

Embodiment 6

FIG. 12 is a configuration diagram illustrating a depth-direction irradiation field enlargement apparatus according to Embodiment 6 of the present invention. A depth-direction irradiation field enlargement apparatus according to Embodiment is different from the depth-direction irradiation field enlargement apparatus 3c in that the former has a plurality of RMW apparatuses whose respective numbers of selectable depths of SOPS are different from one another. A depth-direction irradiation field enlargement apparatus 3d illustrated in FIG. 12 is an example of depth-direction irradiation field enlargement apparatus having two RMW apparatuses 66a and 66b. In the foregoing example, an RMW 35a of the RMW apparatus 66a has more selectable depths of SOPS than an RMW 35b of the RMW apparatus 66b has. An irradiation-field enlargement control apparatus 65 selects the RMW apparatus 66a or the RMW apparatus 66b, which is to be utilized, and also controls a driving device 67a that drives the RMW apparatus 66a and a driving device 67b that drives the RMW apparatus 66b. In response to a signal from an angle sensor 61 of the RMW apparatus 66a or a signal from an angle sensor 61 of the RMW apparatus 66b, the irradiation-field enlargement control apparatus 65 outputs or stops a control signal Sig1.

By increasing the number of pedestals 36 of a blade 37, the number of selectable depths of SOBP can be increased. For example, the RMW 35a has two blades 37a and 37b; each of the blades 37a and 37b has nine pedestals 36a through 36i. In this case, the angle range of each of the blades 37a and 37b is 180°; the angle range of each pedestal is 20°, as is the case with Embodiment 5. It may be allowed that there exists only a single blade 37 and the respective thicknesses of the pedestals 36 of the RMW 35 are different from one another. It may be allowed that also in an embodiment in which the RMW 35 is utilized, the respective thicknesses of the pedestals 36 of the RMW 35 are different from one another.

Because having a plurality of RMW apparatuses 66a and 66b whose respective numbers of selectable depths of SOPB are different from each other, the depth-direction irradiation field enlargement apparatus 3d according to Embodiment 6 can form a wider range of depth of SOPB than the depth-direction irradiation field enlargement apparatus 3c according to Embodiment 5. Accordingly, the particle beam irradiation apparatus 58 having the depth-direction irradiation field enlargement apparatus 3d can form and irradiate more columnar irradiation fields than the particle beam irradiation apparatus 58 according to Embodiment 5 and hence can efficiently perform multi-port irradiation onto the diseased site 40.

Embodiment 7

FIG. 13 is a configuration diagram illustrating a columnar-irradiation-field generation apparatus according to Embodiment 7 of the present invention. A columnar-irradiation-field generation apparatus according to Embodiment 7 is different from the columnar-irradiation-field generation apparatus 4a having the depth-direction irradiation field enlargement apparatus 3c according to Embodiment 5 in that the energy changing apparatus 2 (2a) and the depth-direction irradiation field enlargement apparatus 3c are integrated therein.

The columnar-irradiation-field generation apparatus 4c is provided with range shifters 9a and 9b; RMW apparatuses 66a and 66b; deflection electromagnets 5 and 6 included in a pair of upstream deflection electromagnets that moves the position, of the charged particle beam 1, in the range shifters 9a and 9b and the RMW apparatuses 66a and 66b through which the charged particle beam 1 passes; a first deflection-electromagnet power source 20 that energizes the pair of upstream deflection electromagnets; deflection electromagnets 7 and 8 included in a pair of downstream deflection electromagnets that returns the charged particle beam 1 that has passed through the range shifters 9a and 9b and the RMW apparatuses 66a and 66b onto the original orbit; a second deflection-electromagnet power source that energizes the pair of downstream deflection electromagnets; and a change control apparatus 30 that calculates the amount of movement, of the orbit of the charged particle beam, that is caused by the pair of upstream deflection electromagnets, based on an energy command value inputted from the irradiation control apparatus 33, and transmits an energization current value to the first deflection-electromagnet power source 20. The change control apparatus 30 also controls the second deflection-electromagnet power source 21. In addition, the change control apparatus 30 is provided also with the function of the irradiation-field enlargement control apparatus 65 according to Embodiment 5. The range shifter 9a is disposed at the upstream side of the RMW apparatus 66a in such a way as to be situated between the rotation axle 64a of an RMW 35a and the outer circumference of the RMW 35a. The range shifter 9b is disposed at the upstream side of the RMW apparatus 66b in such a way as to be situated between the rotation axle 64b of an RMW 35b and the outer circumference of the RMW 35b. The operations of the apparatuses are the same as those in Embodiments 1 and 5; thus, explanations therefor will not be repeated.

The range shifters 9a and 9b have the same shape and are formed of the same material; in the foregoing example, the RMW 35a of the RMW apparatus 66a and the RMW 35b of the RMW apparatus 66b are different from each other in terms of the number of selectable depths of SOPB. As explained in Embodiment 6, the RMW 35a of the RMW apparatus 66a can have more selectable depths of SOPB than the RMW 35b of the RMW apparatus 66b.

Because having a plurality of RMW apparatuses 66a and 66b whose respective numbers of selectable depths of SOPS are different from each other, the columnar-irradiation-field generation apparatus 4c according to Embodiment 7 can form a wider range of depth of SOPS than the depth-direction irradiation field enlargement apparatus 3c according to Embodiment 5. Accordingly, the particle beam irradiation apparatus 58 having the depth-direction irradiation field enlargement apparatus 3d can form and irradiate more columnar irradiation fields than the particle beam irradiation apparatus 58 according to Embodiment 5 and hence can efficiently perform multi-port irradiation onto the diseased site 40.

The columnar-irradiation-field generation apparatus 4c according to Embodiment 7 can perform control also in such a way that when the columnar irradiation fields 44 and 45 are formed, the emission and the stop of the charged particle beam 1 are not repeated. For convenience, this example of columnar-irradiation-field generation apparatus will be referred to as a columnar-irradiation-field generation apparatus 4d, in order to distinguish it from the columnar-irradiation-field generation apparatus 4c, explained above. The emission and the stop of the charged particle beam 1 are not repeated when the columnar irradiation fields 44 and 45 are formed, so that there can be performed irradiation of the charged particle beam 1, which is suitable for respiration-synchronized irradiation. For example, the number of pedestals 36 of the RMW 35a is made to be the same as that explained in Embodiment 6, and the number of pedestals 36 of the RMW 35b is made to be the same as that explained in Embodiment 5. When the columnar irradiation fields 44 and 45 are formed, the charged particle beam 1 is made to pass through the pedestal 37 of the RMW 35a or the RMW 35b until the dose is satisfied. As a result, there exists only a single depth of SOBP (SOBP depth a) when the charged particle beam 1 passes through the RMW 35a, and there exists only a single depth of SOBP (SOBP depth b) when the charged particle beam 1 passes through the RMW 35b. On top of that, it is made possible to make SOBP depth b wider than SOBP depth a. Additionally, in the case where the columnar irradiation fields 44 and 45 are formed always without repeating the emission and the stop of the charged particle beam 1, the change control apparatus 30 is not required to generate the control signal Sig1; therefore, the configuration of the change control apparatus 30 can be simplified.

The columnar-irradiation-field generation apparatus 4d according to Embodiment 7 changes the energy of the charged particle beam 1 to desired energy, through two kinds of depths of SOBP; thus, two kinds of columnar irradiation fields can have desired ranges. The emission and the stop of the charged particle beam 1 are not repeated when the columnar irradiation fields 44 and 45 are formed, so that there can be performed irradiation of the charged particle beam 1, which is suitable for respiration-synchronized irradiation. In order to line up many kinds (more than two) of depths of SOBP, it is only necessary to arrange the range filters 9 and the RMW apparatuses 66, the number of each of which corresponds to the number of the kinds of depths of SOBPs.

In each of the columnar-irradiation-field generation apparatus 4c and 4d according to Embodiment 7, there are not provided the pair of upstream electromagnets and the pair of downstream deflection electromagnets for each of the set of the range filter 9a and the RMW apparatus 66a and the set of the range filter 9b and the RMW apparatus 66b, but there is provided only one set of the pair of upstream electromagnets and the pair of downstream deflection electromagnets; therefore, compared with the columnar-irradiation-field generation apparatus 4a according to Embodiment 1, the length of the apparatus in the irradiation direction (Z direction) of the charged particle beam 1 can be shortened.

In the particle beam irradiation apparatus (refer to FIG. 1) having the columnar-irradiation-field generation apparatus 4c or 4d according to Embodiment 7, multi-port irradiation can be implemented based on a treatment plan corresponding to the treatment plan created by the treatment planning apparatus described in Embodiment 1; therefore, as is the case with Embodiment 1, the irradiation flexibility in the depth direction can be raised, without utilizing a bolus. As a result, there can be solved the problem of excess irradiation in IMRT by a particle beam therapy system.

Embodiment 8

Heretofore, the particle beam irradiation apparatuses according to Embodiment 1 through 7 have been explained with a case where the energy of the charged particle beam 1 is changed in the columnar-irradiation-field generation apparatus 4. However, the energy of the charged particle beam 1 can also be changed by changing the parameters for the synchrotron 54. In this embodiment, there will be explained an example where the columnar irradiation fields 44 and 45 are generated by combining the parameters for the synchrotron 54 with the depth-direction irradiation field enlargement apparatus 3. FIG. 14 is a configuration diagram illustrating a particle beam irradiation apparatus according to Embodiment 8 of the present invention. A particle beam irradiation apparatus 60 according to Embodiment 8 is different from the particle beam irradiation apparatuses described in Embodiments 1 through 7 in that the columnar irradiation fields 44 and 45 are generated by making the synchrotron 54 change the energy of the charged particle beam 1, without providing the energy changing apparatus 2 in the columnar-irradiation-field generation apparatus 4.

A columnar-irradiation-field generation apparatus 4 (4e) of the particle beam irradiation apparatus 60 has the depth-direction irradiation field enlargement apparatus 3. The depth-direction irradiation field enlargement apparatus 3 is one of the depth-direction irradiation field enlargement apparatuses 3a, 3b, 3c, and 3d, described above. The irradiation control apparatus 33 outputs an energy command value to the synchrotron 54, which is an accelerator, so that the columnar irradiation fields 44 and 45 are formed at the depth-direction positions thereof planned in a treatment plan. In response to the energy command value, the synchrotron 54 changes the energy of the charged particle beam 1 in accordance with the energy command value. After acquiring predetermined energy, the charged particle beam 1 enters the particle beam irradiation apparatus 60 by way of an ion beam transport system 59. The columnar-irradiation-field generation apparatus 4 (4e) changes the energy of the charged particle beam 1 so that a predetermined depth of SOBP planned in a treatment plan is achieved; predetermined columnar irradiation fields 44 and 45 are formed at a predetermined position in a diseased site 40.

In the particle beam irradiation apparatus 60 according to Embodiment 8, multi-port irradiation can be implemented based on a treatment plan corresponding to the treatment plan created by the treatment planning apparatus described in Embodiment 1; therefore, as is the case with Embodiment 1, the irradiation flexibility in the depth direction can be raised, without utilizing a bolus. As a result, there can be solved the problem of excess irradiation in IMRT by a particle beam therapy system. The particle beam irradiation apparatus 60 demonstrates the effect of the depth-direction irradiation field enlargement apparatuses 3a, 3b, 3c, and 3d, utilized in the columnar-irradiation-field generation apparatus 4 (4e).

Embodiment 9

Embodiment 9 of the present invention is a particle beam therapy system provided with the particle beam irradiation apparatus described in each of Embodiments 1 through 8. FIG. 15 is a schematic configuration diagram illustrating a particle beam therapy system according to Embodiment 9 of the present invention. A particle beam therapy system 51 includes an ion beam generation apparatus 52, an ion beam transport system 59, and particle beam irradiation apparatuses 58a and 58b (60a and 60b). The ion beam generation apparatus 52 includes an ion source (unillustrated), a prestage accelerator 53, and a synchrotron 54. The particle beam irradiation apparatus 58b is provided in a rotating gantry (unillustrated). The particle beam irradiation apparatus 58a is provided in a treatment room where no rotating gantry is installed. The function of the ion beam transport system 59 is to achieve communication between the synchrotron 54 and the particle beam irradiation apparatuses 58a and 58b. A portion of the ion beam transport system 59 is provided in the rotating gantry (unillustrated), and in that portion, there are included a plurality of deflection electromagnets 55a, 55b, and 55c.

A charged particle beam, which is a particle beam such as a proton beam generated in ion source, is accelerated by the prestage accelerator 53 and enters the synchrotron 54. The particle beam is accelerated to have predetermined energy. The charged particle beam launched from the synchrotron 54 is transported to the particle beam irradiation apparatuses 58a and 58b (60a and 60b) by way of the ion beam transport system 59. The particle beam irradiation apparatuses 58a and 58b (60a and 60b) each irradiate a charged particle beam onto a diseased site (unillustrated) of a patient.

In the particle beam therapy system 51 according to Embodiment 9, the particle beam irradiation apparatus 58 (60) is operated based on a treatment plan generated by the treatment planning apparatus described in Embodiment 1, and a charged particle beam is irradiated onto a diseased site of a patient; therefore, the problem of excess irradiation in IMRT by a particle beam therapy system can be solved by raising the irradiation flexibility in the depth direction, without utilizing a bolus.

The particle beam therapy system 51 according to Embodiment 9 irradiates a beam having a columnar dose distribution; therefore, compared with irradiation of a beam having a spot-like distribution, the particle beam therapy system 51 has an advantage in that the irradiation time is shortened. Moreover, multi-port irradiation can be performed; therefore, in the case where irradiation is implemented onto the same diseased site, the damage to the body surface, which is a normal tissue, can be reduced, whereby irradiation can be prevented from being preformed onto a risk site (such as a spinal cord, an eyeball or the like), onto which a particle beam should not be irradiated.

Furthermore, the particle beam therapy system 51 according to Embodiment 9 has an advantage that multi-port irradiation can remotely be performed. Remote multi-port irradiation, which does not require that an engineer or the like enters a treatment room so as to operate the rotating gantry, means that the direction of irradiation onto a diseased site is changed among many directions remotely from the outside of the treatment room and then a particle beam is irradiated. As described above, the particle beam therapy system according to the present invention has a simple irradiation system that requires neither an MLC nor a bolus; therefore, neither bolus replacement work nor MLC-shape confirmation work is required. As a result, there is demonstrated an effect that remote multi-port irradiation can be performed and the treatment time is considerably shortened.

Additionally, as the columnar-irradiation-field generation apparatus 4 having the energy changing apparatus 2 and the depth-direction irradiation field enlargement apparatus 3, there can be utilized the energy changing apparatus 2b described in Embodiment 2 or the depth-direction irradiation field enlargement apparatus 3b described in Embodiment 3.

Heretofore, in Embodiments 5 through 7, there has been explained an example where in order to form a plurality of depths of SOBP, the depth-direction irradiation field enlargement apparatus makes the RMW 35 rotate at a predetermined constant speed and repeats the emission and the emission stop of the charged particle beam 1 in such a way that the charged particle beam 1 passes through only selected pedestals. There exists another way to form a plurality of depths of SOBP by use of the RMW 35. For example, there will be explained a case where there is formed SOBP depth 1, which is a depth of SOBP when the pedestals 36e and 36f are selected. As the motor 62, a servo motor or a stepping motor is utilized. The position of the RMW 35 is set in such a way that the charged particle beam 1 passes through the pedestal 36f, and then irradiation of the charged particle beam 1 is started. After a certain time elapses, the motor 62 sets the position of the RMW 35 in such a way that the charged particle beam 1 passes through the pedestal 36e. After a certain time elapses, the motor 62 sets the position of the RMW 35 in such a way that the charged particle beam 1 passes through the pedestal 36f. By changing the positions of the RMW 35 in such a way that the charged particle beam 1 shuttles between the positions of the pedestal 36e and 36f in a constant cycle, SOBP depth 1 can be formed. In the case where there is formed SOBP depth 5, which is a depth of SOBP when the pedestals 36a through 36f are selected, it is only necessary to change the position of the RMW 35 in such a way that the charged particle beam 1 shuttles between the positions of the pedestals 36a and 36f in a constant cycle. In addition, there may be repeated the procedure in which the charged particle beam 1 is stopped every constant time and then the position, of the pedestal 36, through which the charged particle beam 1 passes through is changed, and after that, the charged particle beam 1 is emitted. The procedure, in which the charged particle beam 1 is not stopped and the position of the RMW 35 is changed in such a way that the charged particle beam 1 shuttles between the positions of the pedestal 36a and 36f, can be applied to respiration-synchronized irradiation.

Various modifications and alterations of this invention will be apparent to those skilled in the art without departing from the scope and spirit of this invention, and it should be understood that this is not limited to the illustrative embodiments set forth herein.

What is claimed is:

1. A particle beam irradiation apparatus having a scanning irradiation system that performs scanning with a charged particle beam accelerated by an accelerator and being mounted in a rotating gantry for rotating the irradiation direction of the charged particle beam, the particle beam irradiation apparatus comprising:
a columnar-irradiation-field generation apparatus for generating a columnar irradiation field by enlarging the Bragg peak of the charged particle beam, said columnar irradiation-field generation apparatus including:
at least one pair of upstream deflection electromagnets and at least one pair of downstream deflection electromagnets, wherein (i) a first deflection electromagnet of the pair of upstream deflection electromagnets deflects the charged particle beam at a predetermined angle with respect to an original beam path and (ii) a second electromagnet of the pair of upstream deflection electromagnets deflects the deflected charged particle beam such that it is parallel with respect to the original beam path,
an energy changing apparatus for changing the energy of the charged particle beam,
a depth-direction irradiation field enlargement apparatus for enlarging the Bragg peak of the charged particle beam, and
a controller that controls the energy changing apparatus in conjunction with the depth-direction irradiation field enlargement apparatus so that the columnar irradiation field of the charged particle beam, entering an irradiation subject from any one of a plurality of different directions, is generated at a depth of the irradiation subject that conforms to a shape of a distal end portion of the irradiation subject.

2. The particle beam irradiation apparatus according to claim 1, wherein the the energy of the charged particle beam is changed by the accelerator.

3. The particle beam irradiation apparatus according to claim 1, wherein the energy changing apparatus comprises:
a range shifter whose thicknesses in directions in which the charged particle beam passes change depending on portions thereof and that reduces the energy of the charged particle beam that passes therethrough, in accordance with the thickness;
a pair of upstream deflection electromagnets, from the at least one pair of upstream deflection electromagnets, that move the passing position, of the charged particle beam, in the range shifter;
a pair of downstream deflection electromagnets, from the at least one pair of downstream deflection electromagnets, that return the orbit of the charged particle beam toward a beam axis along which the charged particle beam has entered the energy changing apparatus; and
a change control apparatus that controls the pair of upstream deflection electromagnets and the pair of downstream deflection electromagnets in such a way that the charged particle beam passes through a predetermined thickness of the range shifter.

4. The particle beam irradiation apparatus according to claim 1, wherein the depth-direction irradiation field enlargement apparatus comprises;
a ridge filter having a thickness distribution in which energy that the charged particle beam loses differs depending on the position thereon through which the charged particle beam passes;
a pair of upstream deflection electromagnets, from the at least one pair of upstream deflection electromagnets, that move the passing position, of the charged particle beam, in the ridge filter;
a pair of downstream deflection electromagnets, from the at least one pair of downstream deflection electromagnets, that return the orbit of the charged particle beam toward a beam axis along which the charged particle beam has entered the depth-direction irradiation field enlargement apparatus; and
an irradiation-field enlargement control apparatus that controls the pair of upstream deflection electromagnets and the pair of downstream deflection electromagnets in such a way that the charged particle beam passes through a predetermined thickness distribution of the ridge filter.

5. The particle beam irradiation apparatus according to claim 1, wherein the depth-direction irradiation field enlargement apparatus comprises;
a plurality of ridge filters, each having a different thickness and each of which changing the energy range of the charged particle beam in accordance with the thickness thereof through which the charged particle beam passes;
a plurality of driving devices for driving the ridge filters respectively; and
an irradiation-field enlargement control apparatus for driving the driving devices so as to control the whole thickness of the ridge filters through which the charged particle beam passes.

6. The particle beam irradiation apparatus according to claim 1, wherein the columnar-irradiation-field generation apparatus comprises;
a range shifter whose thicknesses in directions in which the charged particle beam passes change depending on portions thereof and that reduces the energy of the charged particle beam that passes therethrough, in accordance with the thickness;
a ridge filter that is disposed at the downstream side of the range shifter and has a thickness distribution in which energy that the charged particle beam loses differs depending on the position thereon through which the charged particle beam passes;
a pair of upstream deflection electromagnets, from the at least one pair of upstream deflection electromagnets, that move the passing positions, of the charged particle beam, in the range shifter and the ridge filter;
a pair of downstream deflection electromagnets, from the at least one pair of downstream deflection electromagnets, that return the orbit of the charged particle beam toward a beam axis along which the charged particle beam has entered the columnar-irradiation-field generation apparatus; and
a change control apparatus that controls the pair of upstream deflection electromagnets and the pair of downstream deflection electromagnets in such a way that the charged particle beam passes through respective predetermined thickness distributions of the range shifter and the ridge filter.

7. The particle beam irradiation apparatus according to claim 1,
wherein the depth-direction irradiation field enlargement apparatus comprises;
an RMW apparatus that changes the position thereof, through which the charged particle beam passes, so as to vary the energy of the charged particle beam; and an irradiation-field enlargement control apparatus that controls the RMW apparatus, wherein the RMW apparatus comprises;

an RMW that has an energy absorber in which a plurality of pedestals, the respective axis-direction thicknesses of which are stepwise different from one another, are arranged in the circumferential direction thereof and that varies the energy thereof as the charged particle beam passes through the plurality of pedestals; and a rotation drive device that rotates the RMW, wherein the irradiation-field enlargement control apparatus controls the rotation drive device in such a way that the charged particle beam passes through the plurality of pedestals.

8. The particle beam irradiation apparatus according to claim 7, wherein the depth-direction irradiation field enlargement apparatus comprises an angle sensor that detects a rotation angle of the RMW, and wherein the irradiation-field enlargement control apparatus controls the rotation drive device in such a way that the RMW continues to rotate, and controls the emission start and the emission stop of the charged particle beam, based on the rotation angle detected by the angle sensor, so that the charged particle beam passes through the plurality of pedestals.

9. The particle beam irradiation apparatus according to claim 7, wherein the depth-direction irradiation field enlargement apparatus comprises;

a plurality of RMW apparatuses; and a driving device that moves the RMW apparatus to a position through which the charged particle beam passes or a position through which the charged particle beam does not pass.

10. The particle beam irradiation apparatus according to claim 1, wherein the columnar-irradiation-field generation apparatus comprises;

a range shifter whose thicknesses in directions in which the charged particle beam passes change depending on portions thereof and that reduces the energy of the charged particle beam that passes therethrough, in accordance with the thickness;

an RMW apparatus that is disposed at the downstream side of the range shifter and changes the position thereof, through which the charged particle beam passes, so as to vary the energy of the charged particle beam;

a pair of upstream deflection electromagnets, from the at least one pair of upstream deflection electromagnets, that move the incident position, of the charged particle beam, in the range shifter and the RMW apparatus;

a pair of downstream deflection electromagnets, from the at least one pair of downstream deflection electromagnets, that return the orbit of the charged particle beam toward a beam axis along which the charged particle beam has entered the columnar-irradiation-field generation apparatus; and a change control apparatus that controls the pair of upstream deflection electromagnets and the pair of downstream deflection electromagnets in such a way that the charged particle beam passes through a predetermined thickness of the range shifter, and that performs control in such a way that the RMW apparatus varies the energy of the charged particle beam, wherein the RMW apparatus comprises;

an RMW that has an energy absorber in which a plurality of pedestals, the respective axis-direction thicknesses of which are stepwise different from one another, are arranged in the circumferential direction thereof and that varies the energy thereof as the charged particle beam passes through the plurality of pedestals; and a rotation drive device that rotates the RMW, wherein in order to form a predetermined depth of SOBP, the change control apparatus performs control in such a way that the charged particle beam passes through the plurality of pedestals and wherein the range shifter is disposed at an upstream side of the RMW apparatus in such a way as to be situated between the rotation axle of an RMW and the outer circumference of the RMW.

11. A particle beam therapy system comprising:

an ion beam generation apparatus that generates a charged particle beam and accelerates the charged particle beam by means of an accelerator until the charged particle beam acquires predetermined energy;

an ion beam transport system that transports the charged particle beam accelerated by the ion beam generation apparatus;

a particle beam irradiation apparatus that irradiates the charged particle beam transported by the ion beam transport system onto an irradiation subject; and a rotating gantry that rotates the irradiation direction of the particle beam irradiation apparatus, wherein the particle beam irradiation apparatus is the particle beam irradiation apparatus according to claim 1.

12. The particle beam therapy system according to claim 11, further comprises;

a treatment planning apparatus that generates a treatment plan including the operation conditions of the particle beam irradiation apparatus and the rotating gantry, wherein the treatment planning apparatus comprises;

an irradiation field arranging unit that arranges columnar irradiation fields in accordance with the distal form of an irradiation subject onto which the charged particle beam is irradiated, and arranges columnar irradiation fields in such a way that the columnar irradiation fields cover the inside of the irradiation subject; and an optimization calculation unit that adjusts the arrangement of the columnar irradiation fields in such a way that the irradiation dose onto the irradiation subject falls within a predetermined range, regarding, as the initial state, the state in which the columnar irradiation fields are arranged by the irradiation field arranging unit.

13. The particle beam therapy system according to claim 12, wherein, after arranging the columnar irradiation fields in accordance with the distal form of the irradiation subject, the irradiation field arranging unit arranges the columnar irradiation fields in accordance with the shape of an inner portion, of the irradiation subject, in which the columnar irradiation fields are not arranged.

14. The particle beam therapy system according to claim 12, wherein the irradiation field arranging unit utilizes a plurality of SOBP depths, which are the widths, in the irradiation direction, of the columnar irradiation fields.

15. A particle beam therapy system comprising:

an ion beam generation apparatus that generates a charged particle beam and accelerates the charged particle beam by means of an accelerator until the charged particle beam acquires predetermined energy;

an ion beam transport system that transports the charged particle beam accelerated by the ion beam generation apparatus;

a particle beam irradiation apparatus that irradiates the charged particle beam transported by the ion beam transport system onto an irradiation subject; and a rotating gantry that rotates the irradiation direction of the particle beam irradiation apparatus, wherein the particle beam irradiation apparatus is the particle beam irradiation apparatus according to claim 2.

16. A particle beam therapy system comprising:

an ion beam generation apparatus that generates a charged particle beam and accelerates the charged particle beam by means of an accelerator until the charged particle beam acquires predetermined energy;

an ion beam transport system that transports the charged particle beam accelerated by the ion beam generation apparatus;

a particle beam irradiation apparatus that irradiates the charged particle beam transported by the ion beam transport system onto an irradiation subject; and a rotating gantry that rotates the irradiation direction of the particle beam irradiation apparatus, wherein the particle beam irradiation apparatus is the particle beam irradiation apparatus according to claim 7.

17. A particle beam therapy system comprising:

an ion beam generation apparatus that generates a charged particle beam and accelerates the charged particle beam by means of an accelerator until the charged particle beam acquires predetermined energy;

an ion beam transport system that transports the charged particle beam accelerated by the ion beam generation apparatus;

a particle beam irradiation apparatus that irradiates the charged particle beam transported by the ion beam transport system onto an irradiation subject; and a rotating gantry that rotates the irradiation direction of the particle beam irradiation apparatus, wherein the particle beam irradiation apparatus is the particle beam irradiation apparatus according to claim 8.

18. The particle beam irradiation apparatus according to claim 1, wherein the columnar-irradiation field generation apparatus generates at least two columnar irradiation fields having different SOBP depths and the particle beam irradiation apparatus irradiates the charged particle beam from any one of a plurality of directions in such a way as to generate a largest columnar irradiation field having a largest SOBP at a depth that conforms to the shape of the distal end portion of the irradiation subject.

\* \* \* \* \*